(12) United States Patent
Hafermann et al.

(10) Patent No.: US 10,787,769 B2
(45) Date of Patent: Sep. 29, 2020

(54) FLUORESCENT WHITENING AGENTS AND MIXTURES THEREOF

(71) Applicant: BLANKOPHOR GMBH & CO. KG, Ankum (DE)

(72) Inventors: Marco Hafermann, Bergisch Gladbach (DE); Bernd Hauschel, Bergisch Gladbach (DE); Bernhard Hunke, Hennef (DE); Theo Lansing, Leverkusen (DE); Michael Kraemer, Kürten (DE); Robert Peekhaus, Leverkusen (DE)

(73) Assignee: BLANKOPHOR GMBH & CO. KG, Ankum (DE)

( * ) Notice: Subject to any disclaimer, the term of this patent is extended or adjusted under 35 U.S.C. 154(b) by 64 days.

(21) Appl. No.: 16/099,331

(22) PCT Filed: May 17, 2017

(86) PCT No.: PCT/EP2017/061810
§ 371 (c)(1),
(2) Date: Nov. 6, 2018

(87) PCT Pub. No.: WO2017/198694
PCT Pub. Date: Nov. 23, 2017

(65) Prior Publication Data
US 2019/0194871 A1   Jun. 27, 2019

(30) Foreign Application Priority Data
May 17, 2016   (EP) .................................... 16169981

(51) Int. Cl.
| | |
|---|---|
| *D21H 21/30* | (2006.01) |
| *D21H 21/28* | (2006.01) |
| *D21H 17/07* | (2006.01) |
| *D21H 17/09* | (2006.01) |
| *C09B 23/14* | (2006.01) |
| *C07D 251/70* | (2006.01) |
| *D21H 19/44* | (2006.01) |
| *D21H 23/56* | (2006.01) |

(52) U.S. Cl.
CPC .......... *D21H 21/30* (2013.01); *C07D 251/70* (2013.01); *C09B 23/148* (2013.01); *D21H 17/07* (2013.01); *D21H 17/09* (2013.01); *D21H 19/44* (2013.01); *D21H 21/28* (2013.01); *D21H 23/56* (2013.01)

(58) Field of Classification Search
None
See application file for complete search history.

(56) References Cited

U.S. PATENT DOCUMENTS

| | | | |
|---|---|---|---|
| 3,766,083 A | 10/1973 | Langstroth et al. | |
| 4,468,341 A | 8/1984 | Beyer | |
| 8,740,997 B2 * | 6/2014 | Mahaffey | C11D 3/28 8/648 |
| 2003/0089888 A1 * | 5/2003 | Bacher | D21H 21/30 252/301.21 |
| 2009/0227712 A1 * | 9/2009 | Giesecke | D21H 21/30 524/100 |

FOREIGN PATENT DOCUMENTS

| | | |
|---|---|---|
| EP | 2 302 132 A1 | 3/2011 |
| WO | 2006000327 A2 | 1/2006 |
| WO | 2006026048 A2 | 3/2006 |
| WO | 2009118247 A1 | 10/2009 |

OTHER PUBLICATIONS

International Search Report for PCT/EP2017/061810 dated Jul. 24, 2017 (4 pages).
Written Opinion for PCT/EP2017/061810 dated Nov. 23, 2017 (6 pages).
Examination Report issued in Indian Patent Application No. 201817040849, dated Jul. 3, 2020; 4 pages.

\* cited by examiner

*Primary Examiner* — Dennis R Cordray
(74) *Attorney, Agent, or Firm* — Cantor Colburn LLP

(57) ABSTRACT

Novel fluorescent whitening agents, compositions or mixtures thereof with known fluorescent whitening agents, their preparation, and their use. The novel fluorescent whitening agents (FWAs) contain three structural subunits derived from 4,4'-diamino-2,2'-stilbenedisulfonic acid. The novel compounds and their mixtures with known FWAs show very good effectiveness as fluorescent whitening agents for cellulosic materials, in particular for paper.

24 Claims, No Drawings

FLUORESCENT WHITENING AGENTS AND MIXTURES THEREOF

CROSS REFERENCE TO RELATED APPLICATIONS

This is a U.S. national stage of application no. PCT/EP2017/061810, filed on 17 May 2017. Priority under 35 U.S.C. § 119(a) and 35 U.S.C. § 365(b) is claimed from European Patent Application No. 16169981.4, filed 17 May 2016, the disclosure of which is also incorporated herein by reference.

BACKGROUND OF THE INVENTION

The present invention relates to novel fluorescent whitening agents, compositions or mixtures thereof with other fluorescent whitening agents, their preparation, and their use.

Fluorescent whitening agents (FWAs), also called optical brighteners (OBAs), are well known and are widely used to improve the whiteness and brightness by treatment of cellulose-based materials, like paper, paperboard and cotton. FWAs are also used in detergents to improve the whiteness and brightness of textiles during the washing process. As fluorescent whitening agents for the brightening and whitening of cellulosic materials, derivatives of 4,4'-diamino-2,2'-stilbenedisulfonic acid or a corresponding salt form are known. Typical examples thereof are those derivatives in which 4,4'-diamino-2,2'-stilbenedisulfonic acid is substituted with two triazinyl moieties, and the triazine rings are bearing amino residues. A lot of FWAs having this general structure are known, typical examples are FWAs of the disulpho type, the tetrasulpho type and the hexasulpho type.

Document WO 2006/000327 A2 describes FWAs containing two subunits of 4,4'-diamino-2,2'-stilbenedisulfonic acid.

There is a continuous need to further improve the effectiveness of FWAs.

It has now been surprisingly found that novel FWA compounds and mixtures of the novel FWA compounds with known FWAs show very good effectiveness as FWAs for cellulosic materials, in particular for paper. The novel FWA compounds and mixtures thereof with one or more known FWAs can be formed using the synthesis route for known FWAs by modifying the ratios of the starting components used. The characteristic feature of the novel FWA compounds is that they contain three structural subunits derived from 4,4'-diamino-2,2'-stilbenedisulfonic acid.

Therefore, the invention relates to a compound having the following formula (1):

wherein n=0, 1, or 2; and wherein $R_1$, $R_2$, $R_3$, $R_4$, $R_5$, $R_6$, $R_7$ and $R_8$ independently of each other are H, linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, phenyl substituted with $SO_3^-$, —$(CH_2)_i$—$SO_3^-$, —$(CH_2)_i$-phenyl, —$(CH_2)_k$—COOM, —$(CH_2)_k$—COOR$_9$, —$(CH_2)_k$—CONH$_2$, —$(CH_2)_k$—OR$_9$, wherein i is an integer from 1 to 3, k is an integer from 1 to 4, and $R_9$ is linear or branched $C_1$-$C_3$ alkyl; or $R_1$ and $R_2$, or $R_3$ and $R_4$, or $R_5$ and $R_6$, or $R_7$ and $R_8$ independently of each other together with the nitrogen atom form a morpholine, a piperidine or a pyrrolidine ring; and wherein M represents the corresponding cationic charge equivalent selected from the cations $H^+$, alkali metal cation, $Ca^{2+}$, $Mg^{2+}$, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2, and o≠p, alkyl is linear or branched; and mixtures of said cations.

The invention further relates to a process for preparing a compound of formula (1), comprising the following three steps:

in a first reaction step 2,4,6-trichloro-1,3,5-triazine (cyanuric chloride) is reacted with an aromatic amine of the formula (2) and a compound of formula (3) according to the following reaction scheme, to obtain a mixture of the compounds of formula (5) and formula (6):

Reaction Step 1:

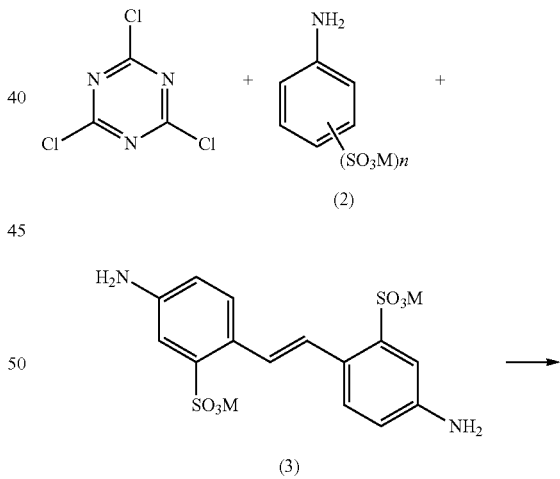

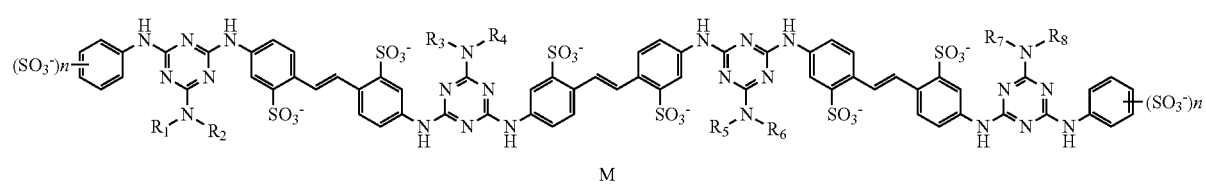

-continued

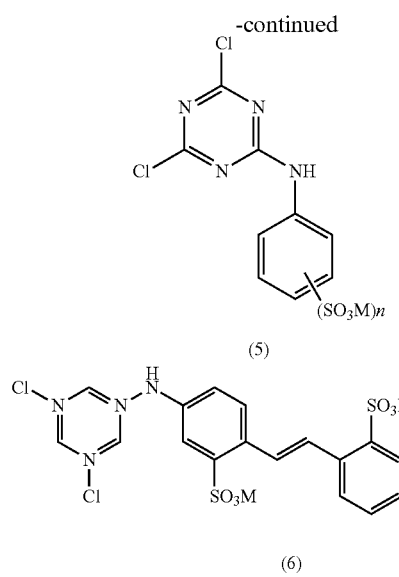

wherein n=0, 1, or 2; and wherein

M represents the corresponding cationic charge equivalent selected from the cations $H^+$, alkali metal cation, $Ca^{2+}$, $Mg^{2+}$, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2, and o≠p, alkyl is linear or branched; and mixtures of said cations;

in a second reaction step the obtained mixture of the compounds of formulae (5) and (6) is reacted with a compound of formula (3) according to the following reaction scheme, to obtain a mixture of the compounds of formula (7) and formula (8), wherein n and M are as defined above:

Reaction Step 2:

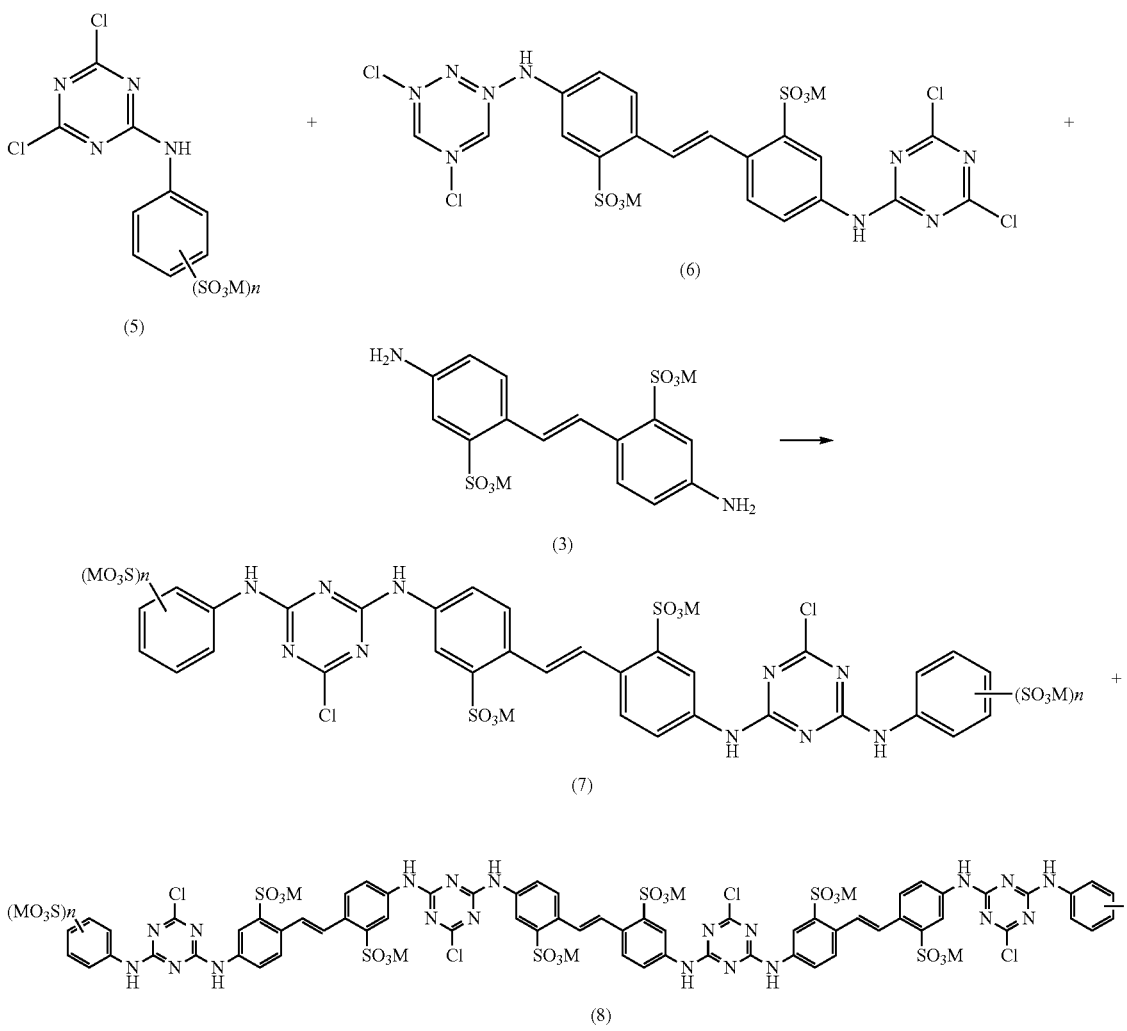

in a third reaction step the obtained mixture of the compounds of formulae (7) and (8) is reacted with at least one amine selected from ammonia, primary and secondary amines, wherein the organic substituents of the primary and secondary amine are selected from linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, phenyl substituted with $SO_3^-$, —$(CH_2)_i$—$SO_3^-$, —$(CH_2)_i$-phenyl, —$(CH_2)_k$—COOM, —$(CH_2)_k$—COOR$_9$, —$(CH_2)_k$—CONH$_2$, —$(CH_2)_k$—OR$_9$, wherein i is an integer from 1 to 3, k is an integer from 1 to 4, and $R_9$ is linear or branched $C_1$-$C_3$ alkyl;

or the substituents of the secondary amine together with the nitrogen atom form a morpholine, a piperidine or a pyrrolidine ring; or a mixture of said amines.

The reaction of the compound of the formula (8) with at least one amine as described above will yield the compound of formula (1).

In a preferred embodiment, the process comprises carrying out the first and second reaction steps as described above, and using an amine of the formula NHR$_x$R$_y$, in the third reaction step, wherein a mixture of the compounds of formula (1a) and formula (10) will be formed as shown by the following reaction step 3:

Reaction Step 3:

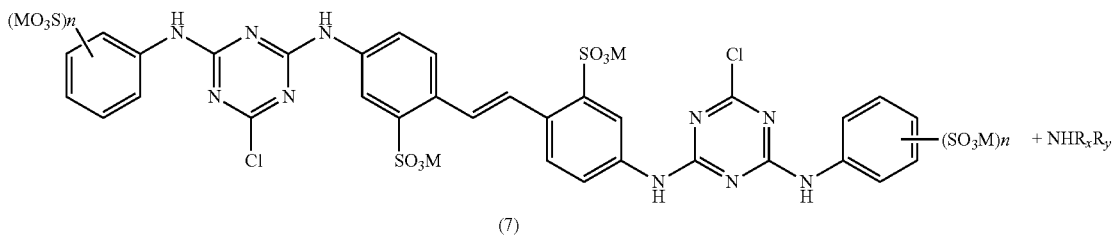

(7)

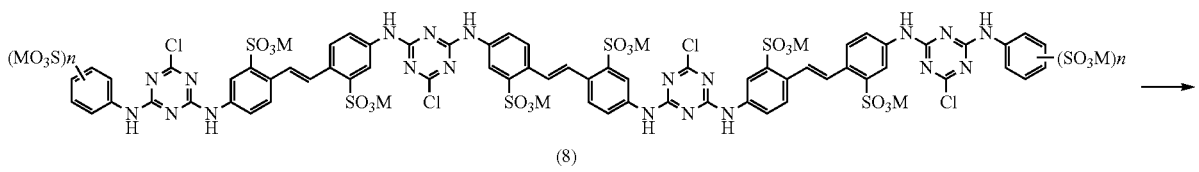

(8)

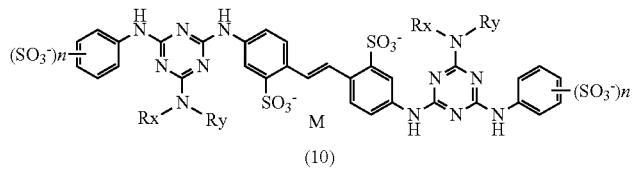

(10)

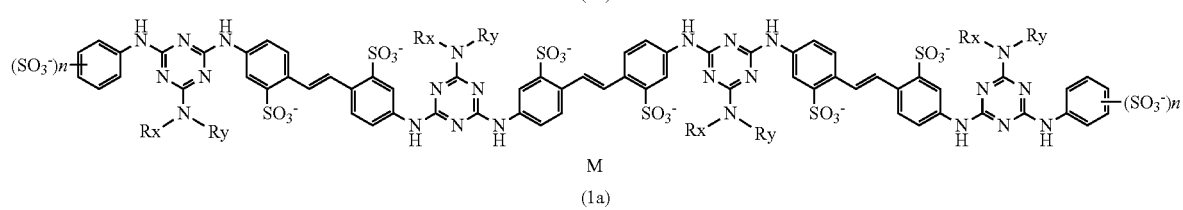

(1a)

wherein n and M are as defined above, and
wherein $R_x$ and $R_y$ independently of each other are H, linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, or
—$(CH_2)_i$—$SO_3^-$, —$(CH_2)_i$-phenyl, —$(CH_2)_k$—$COOM_1$, —$(CH_2)_k$—$COOR_9$, —$(CH_2)_k$—$CONH_2$, —$(CH_2)_k$—$OR_9$, wherein i is an integer from 1 to 3 and wherein k is an integer from 1 to 4, $R_9$ is linear or branched $C_1$-$C_3$ alkyl, or
$R_x$ and $R_y$ independently of each other together with the nitrogen atom form a morpholine, a piperidine or a pyrrolidine ring; or a mixture of said amines.

In exemplary embodiments, in the first reaction step the molar ratio of cyanuric chloride to the compound of formula (2) to the compound of formula (3) is within the range of 1:0.65 to 1.095:0.0025 to 0.15; in the second reaction step the molar ratio of cyanuric chloride to the compound of formula (3) is within the range of 1:0.425 to 0.525; and in the third reaction step the molar ratio of cyanuric chloride to the total amount of amines is within the range of 1:1.00 to 1.50.

The invention further relates to a composition or a mixture comprising at least one compound of formula (1) or formula (1a) and at least one fluorescent whitening agent (FWA) selected from a compound of formula (4) or a compound of formula (9):

hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2 and $o{\neq}p$, and alkyl is linear or branched; and mixtures of said cations.

In exemplary embodiments, in the composition or mixture the compound of formula (1) or formula (1a) is present in an amount of 1 to 90 weight-%, preferably 1 to 50 weight-%, more preferably 1 to 25 weight-%, based on the total amount of the compounds of formulae (1), (1a), (4) and/or (9) in the composition or mixture.

In addition, the invention refers to the use of a compound of formula (1) or (1a) or the above-described composition or mixture for optically whitening cellulose-based materials. The cellulose-based materials can be paper, paperboard, or cellulose-based textiles, e.g. cotton. The compound of formula (1) or (1a) or the above-described composition or mixture can be used or applied by coating application, size press application or wet-end application. The compound of formula (1) or (1a) or the above-described composition or mixture also can be used as additive in detergents.

Furthermore, the invention provides a coating color comprising at least one of a compound of formula (1) or (1a) or the above-described composition or mixture, at least one white pigment, and at least one binder, preferable additionally a co-binder, such as polyvinyl alcohol.

In addition, the invention provides a size press or film press liquor comprising at least one of a compound of

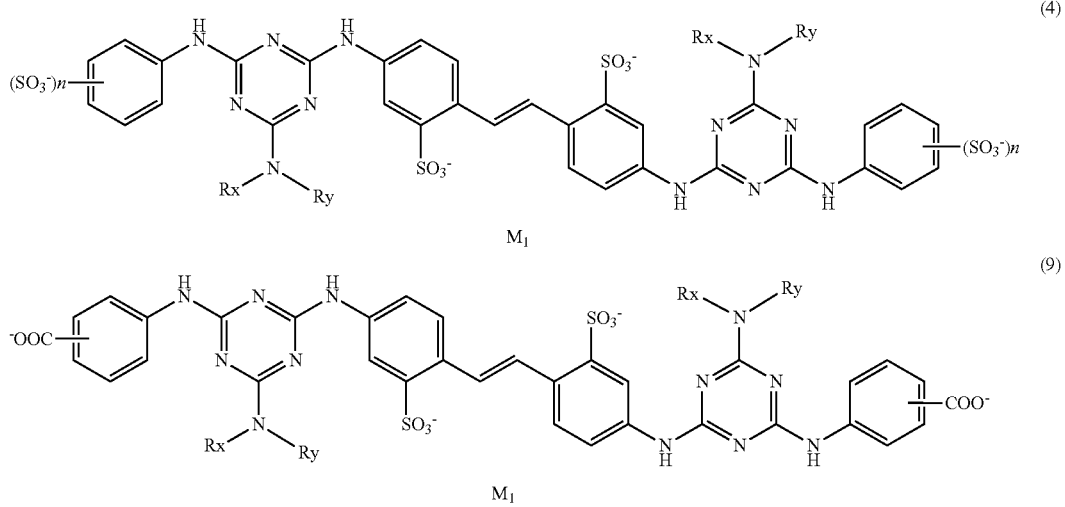

wherein
n=0, 1, or 2,
$R_x$ and $R_y$ independently of each other are H, $C_1$-$C_4$ alkyl, $C_2$-$C_4$ hydroxyalkyl, $C_1$-$C_4$ alkoxyalkyl, $C_2$-$C_4$ cyanoalkyl, wherein the alkyl residue is linear or branched, or —$(CH_2)_i$—$SO_3^-$, —$(CH_2)_i$-phenyl, —$(CH_2)_k$—$COOM_1$, —$(CH_2)_k$—$COOR_9$, —$(CH_2)_k$—$CONH_2$, —$(CH_2)_k$—$OR_9$,
wherein i is an integer from 1 to 3 and wherein k is an integer from 1 to 4, $R_9$ is linear or branched $C_1$-$C_3$ alkyl, or
$R_x$ and $R_y$ independently of each other together with the nitrogen atom form a morpholine, a piperidine or a pyrrolidine ring;
and wherein
$M_1$ represents the corresponding cationic charge equivalent selected from the cations $H^+$, alkali metal cation, $Ca^{2+}$, ammonium, $C_1$-$C_4$ tetraalkyl ammonium, ammonium which is mono-, di-, tri- or tetra-substituted by $C_2$-$C_3$ formula (1) or (1a) or the above-described composition or mixture, and a sizing agent, e.g. starch.

Further, the invention provides the use of a compound of formula (1) or (1a) or an above-described composition or mixture, as additive in detergents.

Further, the invention provides a method for optically whitening cellulose-based materials, comprising treating the cellulose-based materials with at least one of a compound of formula (1) or (1a) or the above-described composition or mixture.

In addition, the invention provides a cellulose-based material obtained or obtainable by the above described method or a cellulose-based material comprising a compound of formula (1) or (1a) or the above-described composition or mixture. The cellulose-based material is in particular paper, paperboard or cellulose-based textile.

Preferred embodiments of the invention are described in the description hereinafter, in the examples, and the claims.

According to the invention the compound of formula (1) has the following formula:

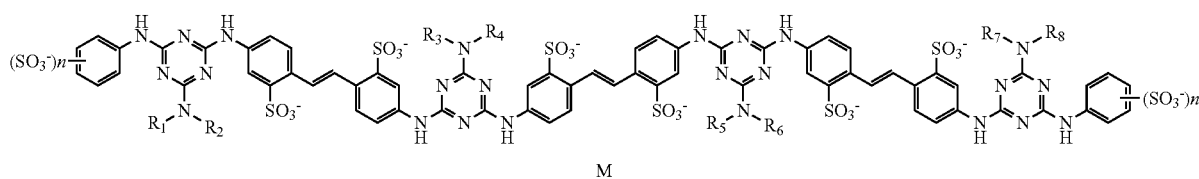

(1)

with n=0, 1, or 2 and wherein $R_1$, $R_2$, $R_3$, $R_4$, $R_5$, $R_6$, $R_7$ and $R_8$ independently of each other mean H, $C_1$-$C_4$ alkyl, $C_2$-$C_4$ hydroxyalkyl, $C_1$-$C_4$ alkoxyalkyl, $C_2$-$C_4$ cyanoalkyl, or phenyl substituted with $SO_3^-$, or —$(CH_2)_i$—$SO_3^-$, —$(CH_2)_i$-phenyl, —$(CH_2)_k$—COOM, —$(CH_2)_k$—$COOR_9$, —$(CH_2)_k$—$CONH_2$, —$(CH_2)_k$—$OR_9$, wherein i is an integer from 1 to 3 and wherein k is an integer from 1 to 4, $R_9$ is $C_1$-$C_3$ alkyl, or $R_1$ and $R_2$ or $R_3$ and $R_4$ or $R_5$ and $R_6$ or $R_7$ and $R_8$ independently of each other together with the nitrogen atom form a morpholine, a piperidine or a pyrrolidine ring;

and wherein

M represents the corresponding cationic charge equivalent selected from the cations $H^+$, alkali metal cation, $Ca^{2+}$, $Mg^{2+}$, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2 and o≠p; as well as mixtures thereof.

Herein, the term "alkyl" means linear or branched alkyl, unless otherwise indicated.

In a preferred embodiment, n is an integer of 1 or 2. In another preferred embodiment, n is 1. In a further preferred embodiment, n is 2. In exemplary embodiments, the substituent —$NR_1R_2$ is identical to —$NR_7R_8$. In other exemplary embodiments, the substituent —$NR_3R_4$ is identical to —$NR_5R_6$. In preferred embodiments, M is selected from $H^+$, $Na^+$, $Li^+$, $K^+$, ammonium, ammonium which is mono, di-, tri- or tetra-substituted by $C_2$-$C_3$ hydroxyalkyl radicals, or mixtures thereof. In another preferred embodiments, n is an integer of 1 or 2, and the substituents $R_1$ to $R_8$ are selected from H, $C_1$-$C_4$ alkyl, $C_2$-$C_4$ hydroxyalkyl, —$(CH_2)_i$—$SO_3^-$, wherein i is an integer from 1 to 3, and phenyl substituted with $SO_3^-$; and M is selected from $H^+$, $Na^+$, $Li^+$, $K^+$, ammonium, ammonium which is mono, di-, tri- or tetra-substituted by $C_2$-$C_3$ hydroxyalkyl radicals; or mixtures thereof. Particularly preferably, $R_1$ to $R_8$ is selected from H, $C_1$-$C_3$ alkyl, $C_2$-$C_3$ hydroxyalkyl, phenyl substituted with $SO_3^-$, and —$CH_2$—$CH_2$—$SO_3^-$.

It is generally known that common FWAs based on one unit of 4,4'-diamino-2,2'-stilbenedisulfonic acid and two triazinyl moieties may be synthesized according to the following sequence in a three-step synthesis. In a first step, 2,4,6-trichloro-1,3,5-triazine (cyanuric chloride) is reacted with an aromatic amine of the formula

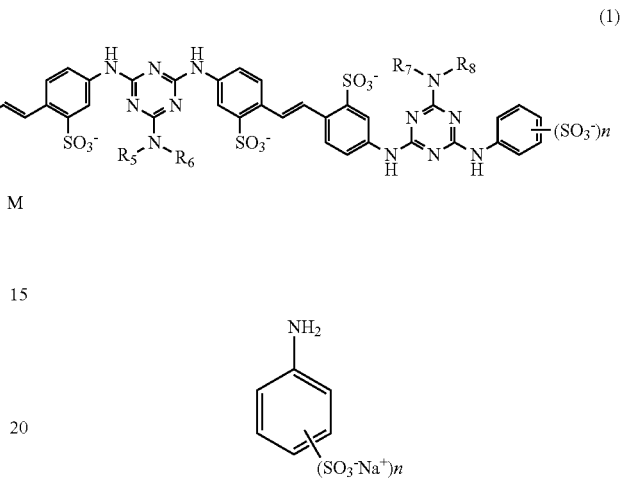

The molar ratio of cyanuric chloride to the amine is typically in the range of 1:0.95-1.10, and n is an integer of 0, 1, or 2.

In a second step, the resulting product of step 1 is then reacted with a compound of the following formula.

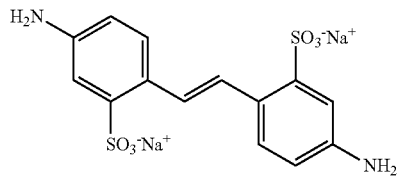

The molar ratio of cyanuric chloride (used in the first step) to said compound in the second step is typically in the range of 1:0.425 to 0.525.

In a third step, the resulting product of step 2 is then reacted with an amine, e.g. diethanolamine or diisopropanolamine.

The molar ratio of cyanuric chloride (used in the first step) to the amount of amine in this third step is typically in the range of 1:1.00 to 1.50.

Suitable reaction conditions, such as temperature, pH, solvents, pressure, and addition of bases to capture and neutralize the generated hydrochloric acid, in order to synthesize FWAs according to this three-step reaction sequence are generally known and e.g. described in WO 2006/000327 A2 and in WO 2009/118247 A1.

It has now been surprisingly found that the FWA compounds of formula (1) can be produced using the above described three-step synthesis modified by adding the compound of formula (3) additionally in the first step. Thus, the invention relates to a process for producing the compound of formula (1) comprising the following three steps. In the first step, cyanuric chloride is reacted with the compounds of formulae (2) and (3) as defined above, which results in the following reaction yielding a mixture of the compounds (5) and (6) formed after completion of the first step:

Reaction Step 1:

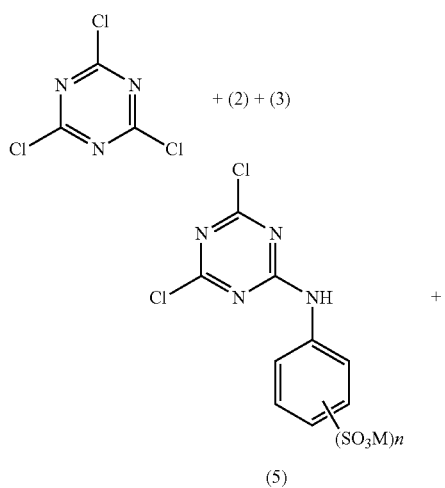

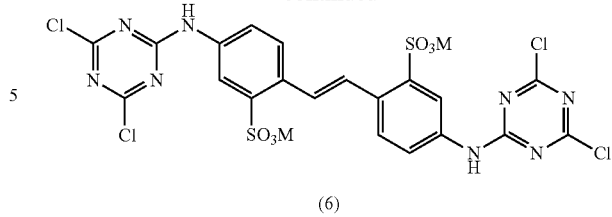

In the first reaction step, the molar ratio of the three reactants cyanuric chloride, compound (2) and compound (3) is preferably in the range of 1:0.65 to 1.095:0.0025 to 0.15, in particular 1:0.70 to 1.09:0.0035 to 0.125. Alternatively, the ratio of cyanuric chloride, compound (2) and compound (3) is preferably 1:0.70 to 0.80:0.10 to 0.15, or from 1:0.80 to 1.08:0.01 to 0.075.

In the second step, the mixture of the compounds (5) and (6) is then reacted with the compound of formula (3) as defined above to yield a mixture as shown by the following reaction scheme.

Reaction Step 2:

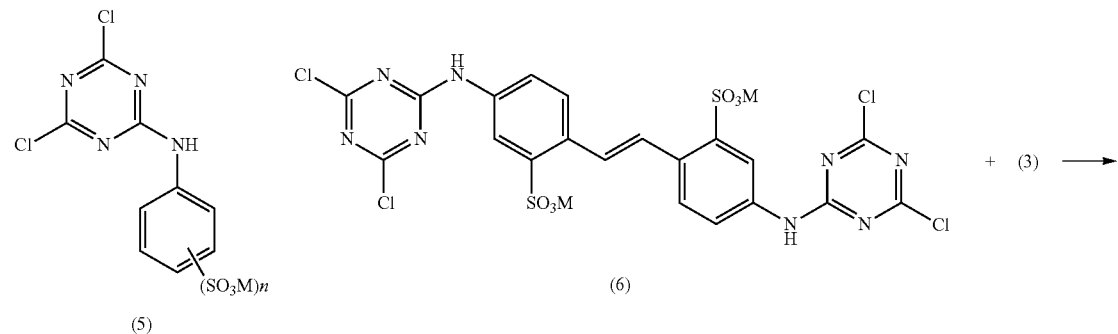

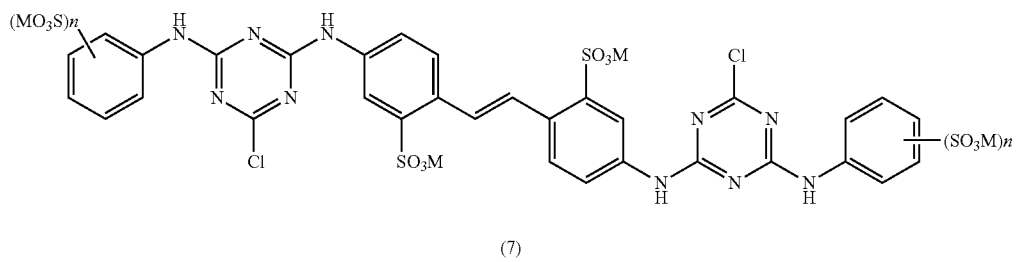

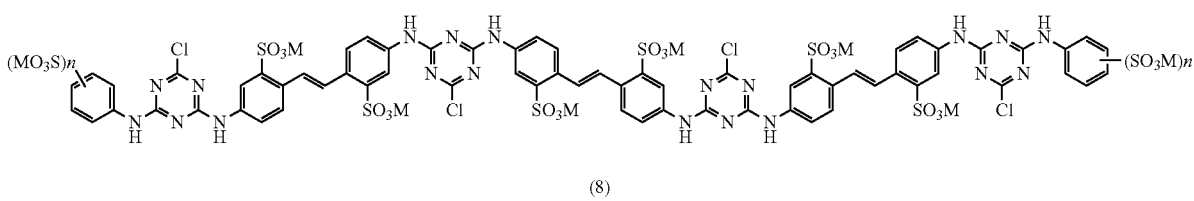

In the second reaction step, the molar ratio of cyanuric chloride to the compound of formula (3) is preferably in the range of from 1:0.425 to 0.525, in particular from 1:0.425 to 0.500. In this, the amount of cyanuric chloride is based on the amount of cyanuric chloride used in the first step.

The resulting mixture of the compounds (7) and (8) is then reacted in the third step with at least one amine selected from ammonia, primary and secondary amines, wherein the organic substituents on the primary and secondary amine are selected from linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, phenyl substituted with $SO_3^{31}$, —$(CH_2)_i$—$SO_3^-$, —$(CH_2)_i$-phenyl, —$(CH_2)_k$—COOM, —$(CH_2)_k$—COOR$_9$, —$(CH_2)_k$—CONH$_2$, —$(CH_2)_k$—OR$_9$, wherein i is an integer from 1 to 3, k is an integer from 1 to 4, and $R_9$ is linear or branched $C_1$-$C_3$ alkyl;

or the substituents on the secondary amine together with the nitrogen atom form a morpholine, a piperidine or a pyrrolidine ring. Also a mixture of said amines can be used in the third reaction step.

In the third step, the amine, such as NHR$_x$R$_y$, will substitute the chlorine residues in the compounds of the formulae (7) and (8). In this third step, the molar ratio of cyanuric chloride to the total amount of amines is preferably in the range of from 1:1.00 to 1.50, in particular from 1:1.00 to 1.25. In this, the amount of cyanuric chloride is based on the amount of cyanuric chloride used in the first step.

The mixture obtained after the third reaction step contains the compound of formula (1).

As an exemplary embodiment, when carrying out the first and second reaction steps, and using the amine NHR$_x$R$_y$ in the third reaction step, a mixture of the compounds (1a) and (10) will be formed as shown by the following reaction scheme.

Reaction Step 3:

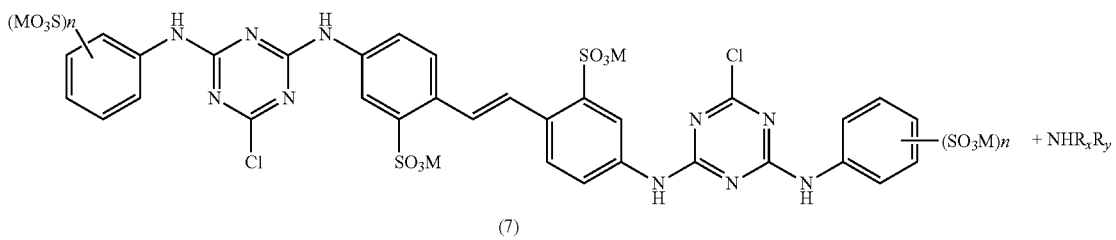

(7)

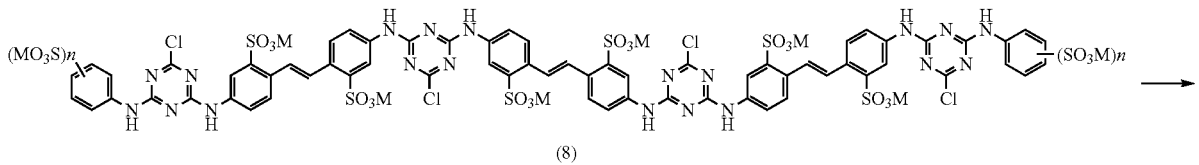

(8)

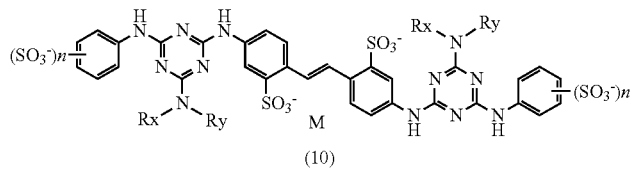

(10)

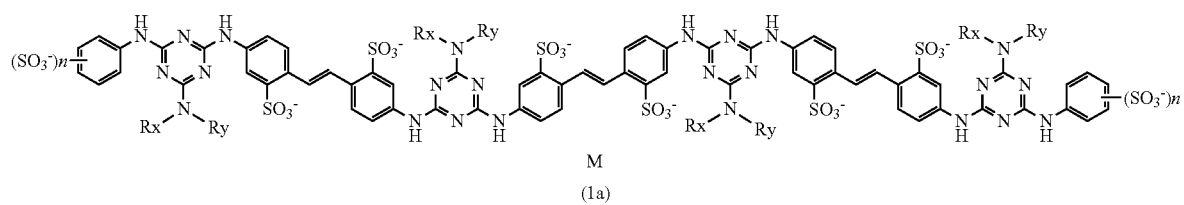

(1a)

The compound of formula (1) represents the compound of formula (1a), if in formula (1) the residues $R_1$ to $R_8$ have the same meaning as $R_x$ and $R_y$ in formula (1a). Thus, the mixture obtained after the third reaction step contains the compound of formula (1) when the residues $R_x$ and $R_y$ of formula (1a) have the same meaning as the residues $R_1$ to $R_8$ of formula (1).

The mixture obtained after the third reaction step can be further worked up or processed by known methods to obtain the compound of formula (1) or formula (1a) in purer form, e.g. by means of fractionated crystallization or preparative liquid chromatography. In alternative embodiments, the mixture obtained after the third reaction step is used as FWA without further purification or work-up.

The compound of formula (1) or (1a) can be used alone as an FWA or it can be used in combination with one or more known FWAs being suitable for the fluorescent whitening of cellulosic materials, e.g. paper. Suitable FWAs are one or both of the following formulae:

molar ratio of cyanuric chloride to compound (2) and compound (3) is in the range of 1:0.775 to 1.09:0.0075 to 0.10. The molar ratios used during the second and third reaction step can be selected as mentioned above.

Suitable reaction conditions for the first reaction step are the following conditions. The first step may be carried out at atmospheric pressure or at elevated pressure up to 10 bar, preferably the reaction is carried out at atmospheric pressure. Cyanuric chloride may be reacted as a dispersion in water, optionally with the addition of surfactants. Cyanuric chloride may be also reacted as solution in an organic solvent, preferably acetone or methylethylketone. A mixture of water and an organic solvent may be used as well. Preferably, the reaction is carried out in water without addition of organic solvents. The reaction is carried out at temperatures between −10° C. and 30° C. In a preferred embodiment, when the reaction is carried out in water, the temperature range is between 0° C. and 30° C. The reaction is preferably carried out at acidic to neutral conditions,

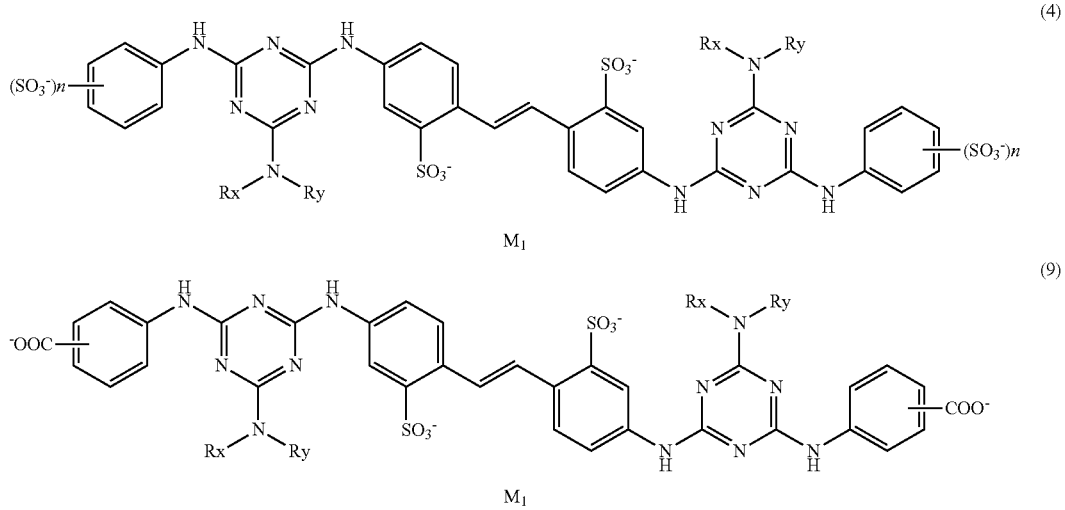

Such known FWAs that can be mixed with the compound of formula (1) or (1a) are e.g. those falling under formula (4) or formula (9) as described above. Suitable FWAs are described in EP 2 302 132 and EP 2 478 153. The mixing ratio can be selected such that 1 to 50 weight-% of the compound of formula (1) or (1a) is present in the mixture, preferably 1 to 25 weight-% of the compound of formula (1) or (1a), based on the total amount of FWA compounds in the mixture.

It is also possible to produce the compound of formula (1) or (1a) in a mixture obtained after the third reaction step with a targeted molar ratio of the components and to use this mixture for fluorescent whitening and brightening purposes without separation of the compound of formula (1) or (1a) or further purification. In an exemplary embodiment, it is possible to prepare the compounds of the formulae (1a) and (10) with a targeted ratio of both compounds, and to use the resulting mixture for fluorescent whitening and brightening purposes without separation of the compounds (1a) and (10). To obtain the targeted ratio, the ratio can be varied by selecting the amounts of the compounds (2) and (3) used in the first step. Preferably, the molar ratio of cyanuric chloride to compound (2) and compound (3) is then in the range of 1:0.70 to 1.09:0.0035 to 0.125. Particularly preferably, the preferably at a pH range of from 2.0 to 7.0. The compounds of formulae (2) and (3) are preferably added as alkali metal salts in the form of their aqueous solutions. The reaction pH is controlled by adding a suitable base, selected from hydroxides, hydrogen carbonates or carbonates of alkali metals, and tertiary aliphatic amines, or mixtures thereof. Trace amounts of $Ca^{2+}$ and/or $Mg^{2+}$ which naturally occur in water may be present during the synthesis as introduced by the used water.

The second and third reaction steps can be carried out by usual methods of synthesizing FWAs based on 4,4'-diamino-2,2'-stilbenedisulfonic acid. These methods are known by persons skilled in the art, and are e.g. described in WO 2006/000327 A2 and in WO 2009/118247 A1.

A suitable method to analyze the resulting product mixture is High Performance Liquid Chromatography (HPLC) with detection at 350 nm wavelength. The relative abundance of a compound in the HPLC chromatogram is expressed as area-%, provided that all detected peaks sum up to 100%. Preferably, the compound of formula (1) or (1a) is detected in an amount of 1 to 35% and the compound of formula (10) is detected in an amount of 60 to 95% in the resulting product mixture.

The resulting preparations or solutions from the three-step synthesis process contain a mixture comprising the compound of formula (1) or (1a) and e.g. compound of formula (10), preferably in form of their salt forms, as described above. These preparations or solutions can be further worked up either by a membrane filtration process, wherein the FWA solution is concentrated and inorganic salts are removed to a large extent. The workup steps can also involve the precipitation or crystallization of the FWA compounds from the aqueous solution by means of acid addition or salt addition, and the subsequent isolation of the FWA compounds by filtration. The obtained filter cake, preferably after washing, may be formulated as slurry or as aqueous solution of the corresponding FWA compounds, optionally under addition of bases, solubilizing additives and/or carrier polymers. Those additives may be also added to the FWA concentrates obtained by membrane filtration. Another option is the spray drying of aqueous FWA solutions in order to produce dry powders.

The liquid preparations obtained after workup or formulation preferably have an FWA content in the range of 8 to 30 weight-%, in particular 10 to 25 weight-%, based on 100 weight-% of the liquid preparation.

The FWA preparations can contain organic by-products and inorganic salts arising from the synthesis. Suitable solubilizing additives are urea, alcohols and amines, for example diethylene glycol, diethylene glycol monomethylether, diethylene glycol monoethylether, triethylene glycol, propanediol, glycerol, ε-caprolactam, 2-(dimethylamino) ethanol, monoethanolamine, diethanolamine and triethanolamine.

The invention also relates to a composition or a mixture comprising at least one, e.g. one or two, of compound of formula (1) or (1a) and at least one, e.g. one or two, of known fluorescent whitening agents (FWAs). In exemplary embodiments, the composition or mixture comprises one compound of formula (1) or (1a) and one known fluorescent whitening agent (FWA). The known FWA can be the compound of formula (4) or (9) as described above. The composition or mixture is preferably used in form of a liquid FWA preparation.

The liquid FWA preparations may contain carrier polymers in order to suppress the association between FWA molecules and to increase the solubility of the contained FWA compounds. Suitable carrier polymers are polyethylene glycol, polyvinyl alcohol, carboxymethyl cellulose, polyvinylpyrrolidone, or combinations thereof. Preferred carrier polymers are linear polyethylene glycols with an average molecular weight $M_n$ in the range of 200 to 8000 g/mol, and polyvinyl alcohols with a degree of hydrolysis of from 80 to 99% and an average molecular weight $M_w$ of from 10 000 to 150 000 g/mol. The amounts of polyethylene glycol in the liquid formulation are preferably chosen between 1 and 40 weight-%, whereas the amounts of polyvinyl alcohol are preferably chosen between 1 and 20 weight-%. In addition, the liquid FWA preparations may contain biocides, providing stabilization against the growth of bacteria and fungi. Furthermore, the pH of the liquid FWA preparations may be adjusted to the desired value by adding common acids or bases, wherein suitable pH values are in the range of from 6 to 10.

The compound of formula (1) or (1a) or the novel FWA mixtures or compositions according to the present invention can be used to improve the whiteness and brightness of cellulose-based materials like paper, paperboard and textiles made from cotton. They also can be used as an additive to detergents.

A large variety of papers is suitable for whitening in the context of the present invention: paper made from unbleached or bleached chemical, semi-chemical or mechanical pulp, e.g. chemical short fiber and long fiber pulp, groundwood, thermo-mechanical pulp (TMP) and chemi-thermo mechanical pulp (CTMP). Also paper made from unbleached or bleached deinked pulp (DIP) is suitable. DIP is produced from recovered paper. In papermaking, it is often the case that different grades of mechanical, semi-chemical and chemical pulp as well as recycled pulp are combined in order to impart certain properties to the paper. Also the use of inorganic fillers besides cellulose pulp is common in papermaking, on one hand this leads to overall lower cost of the paper raw materials, on the other hand, fillers lead to an improvement of important functional properties of the paper, like basic brightness, opacity and printability. All papers filled with the commonly used fillers are suitable for whitening in the context of the present invention, e.g. papers filled with GCC (ground calcium carbonate), kaolin, PCC (precipitated calcium carbonate), titanium dioxide, talc, barium sulfate, calcium to sulfate and satin white.

The compounds of formula (1) or (1a) or the novel FWA mixtures according to the present invention can be used for coating application. The invention also comprises coating colors, or coating slips, or coating compositions comprising the compounds of formula (1) or (1a) or the novel FWA mixtures according to the present invention. In a preferred embodiment, the compounds of formula (1) or (1a) or the novel FWA mixtures according to the present invention are used for the whitening of uncoated paper or board, in particular of printing and writing papers, folding boxboard and white-top linerboard. In another preferred embodiment, the compounds of formula (1) or (1a) or the novel FWA mixtures according to the present invention are used for the whitening of coated paper or board. Generally, all coated paper grades are suitable, since coating colors for coated printing paper as well as for coated packaging board are typically based on white pigments, and thus the fluorescent whitening of the coating color is generally desirable and leads to improved whiteness.

In a further preferred embodiment, the compounds of formula (1) or (1a) or the novel FWA mixtures according to the present invention are used for the fluorescent whitening of cellulosic textiles, wherein cotton fabric is preferred. In still another embodiment, the compounds of formula (1) or (1a) or the novel FWA mixtures according to the present invention are used as detergent additive, wherein detergents in powder form are preferred. The invention also comprises detergents comprising the compounds of formula (1) or (1a) or the novel FWA mixtures according to the present invention.

The compounds of formula (1) or (1a) or the novel FWA mixtures can be added in several ways during the papermaking process: in a pulp preparation stage or in the paper machine wet end, during the surface treatment of the formed paper web, or to the coating color. Also a combination of two or more thereof is possible.

The compounds of formula (1) or (1a) or the novel FWA mixtures according to the present invention can be used for wet end application. The wet end addition of the compounds or novel FWA mixtures may take place in undiluted or diluted to form, to the thick stock or to the thin stock. Suitable addition rates of a liquid FWA formulation according to the present invention are between 0.05 and 2.5 weight-%, related to dry paper weight.

The compounds of formula (1) or (1a) or the novel FWA mixtures according to the present invention can be used for size press application or sizing of paper. The invention also comprises size press or film press liquors comprising the compounds of formula (1) or (1a) or the novel FWA mixtures according to the present invention. The surface treatment, respectively surface sizing of uncoated paper with the size press or film press liquors according to the invention is usually carried out with an application device that is part of the paper machine. Suitable surface treatment devices are all customary devices that are used in the paper industry for surface sizing, for example the size press and the film press. The size press or film press liquors are preferably based on starch solutions, wherein the starch concentration ranges up to 15 weight-%. The liquors also can be based on dextrin, wherein the concentration of the liquor can be even higher. Dextrin is thermally degraded starch having a relatively low molecular weight. Suitable starches are preferably starches derived from potatoes, wheat, maize, tapioca, rice, pea, and mixtures thereof. It is possible to use native starches for the surface sizing process, but preferably degraded or derivatized starches are used. The starch degradation can take place by oxidative treatment, e.g. with hypochlorite, by enzymatic, thermal or chemical treatment. Suitable starch derivatives for the size press or film press liquor are e.g. cationized starches, cationized starches that have been additionally degraded by oxidation, and hydroxyalkyl substituted starches. Furthermore the size press or film press liquor can contain inorganic salts, e.g. to adjust the conductivity of the paper, or to influence its printing properties positively, e.g. for inkjet printing. Examples for suitable inorganic salts are sodium chloride, sodium sulfate, calcium chloride, magnesium chloride, calcium formate and magnesium formate. The surface treatment of uncoated paper using the size press or film press liquor of the invention can be carried out with water-soluble calcium or magnesium salts, in order to improve color fixation during inkjet printing, as well as to get a quick uptake of the liquid from the inkjet ink. This in turn leads to an improved inkjet print image regarding color density, brilliancy and edge sharpness.

Furthermore, the size press or film press liquors can contain defoamers and synthetic sizing agents. These sizing agents are applied to adjust the paper's uptake of water-based liquids during the writing and printing process in a controlled manner. Suitable synthetic surface sizing agents are polymer dispersions and polymer solutions, which are containing polymers of the styrene-acrylic ester type, the styrene-acrylic acid type and the styrene-maleic anhydride type. Further suitable is alkylketene dimer (AKD), which may be used as such or in combination with the above mentioned sizing polymers. Optionally, the size press or film press liquor may also contain additives to impart special functional properties to the treated paper, like barrier effects and oleophobic behavior. Such additives can be fluorocarbons, waxes or other paper additives that lead to barrier properties. Furthermore, carrier polymers can be added to the size press or film press liquors, with the aim to reduce the association tendency between FWA molecules and to increase the greening limit, for example by adding linear polyethylene glycol or polyvinyl alcohol.

The liquid FWA formulations used according to the present invention can be added to the size press and film press liquors, respectively, according to the invention in the range of from 0.1 to 5 weight-%, related to the total amount of liquor.

Coating colors according to the present invention can be based on white pigments and binders, such as are common paper coating colors,. Examples for suitable white pigments to produce the coating colors are GCC, kaolin respectively clay, calcined clay, PCC, talc, titanium dioxide and calcium sulfate. Examples for suitable binders are, on one hand, polymer dispersions, respectively latices, based on polymers of the types of styrene-butadiene, styrene-acrylic ester, vinyl acetate and vinyl acetate-acrylic ester. On the other hand, modified starches and dextrins can be used binders as well, also in combination with the above mentioned polymer dispersions. In some cases, casein can be used as binding agent. The coating colors furthermore can contain co-binders, e.g. polyvinyl alcohol and carboxymethyl cellulose. Preferably, polyvinyl alcohol is used as co-binder. Additionally, dispersing agents may be added to the coating color in order to stabilize the pigment particles, wherein the major part of dispersing agent already may be contained in the pigment slurry that is used as starting material to prepare the coating color. But it is also possible to start from the white pigments in dry form. In this case, the first step of the coating color preparation is preferably the dispersion of the white pigments to form the corresponding pigment slurries. Thereafter, the blending of the components of the coating color is started. The coating color according to the invention can contain dispersing agents. Suitable dispersing agents are polyacrylic acid or modified polyacrylic acid in form of their salts, oligophosphates and polyphosphates. Moreover, the coating colors preferably contain thickening substances, in order to adjust a certain desired viscosity, needed for the further processing, and also a certain degree of water retention. Examples for suitable thickeners are carboxymethyl cellulose, alginates, or fully synthetic thickener polymers based on acrylates. Further,as coating color additives, tinting dyes or tinting pigments, defoamers and optionally stearates, can be used.

The liquid FWA formulations used according to the present invention are preferably added to the coating colors in an amount of 0.05 to 3.5 weight-% and preferably between 0.1 and 2 weight-%, related to the total pigment weight in the coating color.

The coating colors of the invention can be applied by commonly used paper coating processes, suitable applications are, for example film press coating, blade coating, curtain coating and spray coating.

The compounds and novel FWA mixtures according to the present invention are preferably used for the whitening and brightening of coated paper, e.g. by using them as coating color additive as described above. It is particularly preferred to use them in coating colors that are containing polyvinyl alcohol as cobinder.

The term paper coating is normally used, once the coating color forms a fully closed layer on the base paper, this is normally the case above a coat weight of about 5 to 6 g/m$^2$. Besides the paper coating process, the term pigmentation describes also a common process, wherein the paper surface is treated in a similar way to the above described surface sizing process, but with the difference that pigments are an essential part of the treatment liquor, optionally combined with further binders besides starch. The coat weight during the pigmentation process is preferably below 5-6 g/m$^2$. The pigmentation of a given base paper is typically used to improve its optical properties, as well as the printability and the evenness of the paper surface. The compounds and novel FWA mixtures according to the present invention can be used in a pigmentation process and corresponding treatment liquors, in order to achieve an increase of brightness and whiteness. The invention also comprises pigmentation treatment liquors comprising the compounds of formula (1) or (1a) or the novel FWA mixtures according to the present invention.

The invention also provides cellulose-based materials produced by the above described processes or cellulose-based materials comprising the compounds or FWA composition or mixture as described above. The cellulose-based material is in particular paper, paperboard or cellulose-based textile, e.g. cotton.

The examples hereinafter illustrate the invention without restricting the scope of protection.

EXAMPLES

General Preparation Conditions

A 4 l glass reactor equipped with a cooling and heating jacket connected to a thermostate, a propeller stirrer and a pH electrode was used for all preparation examples. Softened water was used for all preparation examples 1-4.

4-aminobenzenesulfonic acid (trivial name: sulfanilic acid) was first transferred into its sodium salt form by dissolving it in water at ambient temperature under stirring while adding 1 equivalent sodium hydroxide. A solution of sodium hydroxide with 10.4% strength was used for this purpose. Stirring was continued until a clear solution was obtained.

The resulting solution of sodium sulfanilate had a content of 0.93 mol/kg.

To 554.8 g of this solution, excess NaOH and water was added in the following amounts:

131.4 g of water and 204.8 g of a NaOH solution with 10.4% strength were added at ambient temperature under stirring. After the addition, stirring was continued for another 10 minutes. 891 g of a sodium sulfanilate solution with excess NaOH were obtained, containing 0.516 mol sodium sulfanilate and 0.532 mol NaOH (solution 1).

4,4'-diamino-2,2'-stilbenedisulfonic acid (trivial name: DAS) was first transferred into its sodium salt form by dissolving it in water at ambient temperature under stirring while adding 1 equivalent sodium hydroxide. A solution of sodium hydroxide with 10.4% strength was used for this purpose. Stirring was continued until a clear solution was obtained.

The resulting solution of the DAS disodium salt had a content of 0.401 mol/kg (solution 2).

General Analytical Conditions

Extinction value: The obtained FWA solutions were characterized by measuring their extinction in a 1 cm cuvette at 350 nm, using an Uvikon XS spectrophotometer. Diluted samples containing 0.01 weight-% of the FWA solution were prepared prior to each measurement using demineralized water. The measured extinction value was then calculated back to a hypothetical aqueous solution containing 1.00 weight-% of the original FWA solution, the thus obtained value is called $E_{1/1}$ value.

HPLC: The obtained FWA solutions were analyzed with a HPLC device from Shimadzu, the peak detection took place at 350 nm. All detected peaks were summed up to 100 area-%.

Preparation examples 1-3: the main component, representing the FWA molecule of formula (10) with n=1, $R_x$ and $R_y$=$CH_2CH_2OH$ and M=$Na^+$, had a retention time of approx. 26 minutes. The FWA compound represented by formula (1) with n=1, $R_1$ to $R_8$=$CH_2CH_2OH$ and M=$Na^+$, had a retention time of approx. 45 minutes.

Preparation example 4: the main component, representing the FWA molecule of formula (10) with n=1, $R_x$ and $R_y$= [$CH_2CH(CH_3)OH$] and M=$Na^+$, led to 3 HPLC peaks, as it is present in the form of different isomers. These 3 peaks had a retention time of 31-32 minutes. The FWA compound represented by formula (1) with n=1, $R_1$ to $R_8$=[$CH_2CH(CH_3)OH$] and M=$Na^+$, had a retention time of approx. 49 minutes.

Preparation Example 1

Reaction Step 1:

650 g of water were added to the reactor and the stirrer was started. Stirring was maintained through the course of the whole synthesis. 11.0 g of sodium chloride and 0.1 g of $NaHCO_3$ were added and dissolved under stirring. The mixture was then cooled to 8° C. Then, 1.0 g of the dispersant DIADAVIN® CA 40130 (from LEVACO Chemicals GmbH) were added and mixed in during 1 minute of continued stirring.

100.0 g of cyanuric chloride (0.542 mol) were then added to the reactor, followed by the addition of 100.0 g of water, which had a temperature of 8° C. Stirring was continued for 30 minutes to disperse the cyanuric chloride in water. The temperature was maintained at 8° C. and the pH remained in the range of 5.5 to 7.0.

Then, 16.3 g of solution 2 (containing 0.0065 mol of DAS disodium salt) were added to the reactor with constant speed during 10 minutes. The pH in the reaction mixture was kept in the range of 3.8-4.5 by simultaneous addition of a NaOH solution with 10.4% strength. After completion of the addition of solution 2, the pH was adjusted to a value in the range of 4.3-4.7 with the NaOH solution. 5.1 g of the NaOH solution were added in total during and after addition of solution 2.

Then, the addition of sodium sulfanilate solution containing excess NaOH (solution 1) was started. 891 g of solution 1 (containing 0.516 mol sodium sulfanilate) were added with constant speed over 2 hours and 30 minutes. The reaction temperature was allowed to raise to 16° C. during the first hour of addition, then the temperature was kept at 16° C. for the rest of the addition time. The pH in the reaction mixture maintained between 4.0 and 5.0 during the whole addition time.

After completion of the addition, stirring was continued for another 20 minutes and then the temperature was raised to 20° C.

Reaction Step 2:

654.7 g of solution 2 (containing 0.263 mol of DAS disodium salt) were added with constant speed over 30 minutes. During this addition of solution 2, the pH in the reaction mixture was raised to 6.5 and then kept at this value through addition of a NaOH solution with 10.4% strength. The temperature was maintained between 20-25° C. during the addition of solution 2. After completion of the addition, the temperature was raised to 65° C. during 1 hour and 15 minutes and then kept for another 1 hour and 20 minutes, while the pH was still maintained at 6.5 through addition of the NaOH solution. In total, 205.4 g of the NaOH solution with 10.4% strength were added during this reaction step.

Reaction Step 3:

76.3 g of an aqueous solution of diethanolamine, having an active content of 89.6 weight-%, were added to the reaction mixture with constant speed during 9 minutes. The temperature was then raised to 100° C. during 45 minutes. The reaction started at approx. 75° C., this led to a drop of pH. When the pH value had reached 8.0, the addition of a NaOH solution with 10.4% strength was started and the pH was maintained at 8.0 through addition of this solution. After reaching 100° C., stirring was continued for further 3 hours while the pH was still maintained at 8.0. In total, 179.7 g NaOH solution were added during this step. The resulting FWA solution was then cooled to 55° C., filtered through a fluted paper filter, and allowed to cool furthermore down to 25° C.

The resulting yellowish FWA solution had an $E_{1/1}$ value of 57.

HPLC analysis gave the following results: the main component according to the general formula (10) with n=1, $R_x$ and $R_y$=$CH_2CH_2OH$ and M=$Na^+$ was detected with 91.1%. The FWA according to the general formula (1) with n=1, $R_1$ to $R_8$=$CH_2CH_2OH$ and M=$Na^+$ was detected with 4.3%.

Preparation Example 2

The procedure as described in preparation example 1 was repeated with the following changes:
Reaction Step 1:
65.2 g of solution 2 (containing 0.0261 mol of DAS disodium salt) and 845 g of solution 1 (containing 0.490 mol sodium sulfanilate) were used. 20.5 g of a NaOH solution with 10.4% strength were added during and directly after the addition of solution 2 to adjust the pH to 4.3-4.7.
Reaction Step 2:
648.0 g of solution 2 (containing 0.260 mol of DAS disodium salt) were used. In total, 204.1 g of NaOH solution were added during this step.
Reaction Step 3:
In total, 169.3 g of NaOH solution were added during this step.

The resulting yellowish FWA solution had an $E_{1/1}$ value of 59.

HPLC analysis gave the following results: the main component according to the general formula (10) with n=1, $R_x$ and $R_y$=$CH_2CH_2OH$ and M=$Na^+$ was detected with 80.0%. The FWA according to the general formula (1) with n=1, $R_1$ to $R_8$=$CH_2CH_2OH$ and M=$Na^+$ was detected with 11.7%.

Preparation Example 3

The procedure as described in preparation example 1 was repeated with the following changes:
Reaction Step 1:
130.2 g of solution 2 (containing 0.0522 mol of DAS disodium salt) and 752.6 g of solution 1 (containing 0.436 mol sodium sulfanilate) were used. 40.9 g of a NaOH solution with 10.4% strength were added during and after the addition of solution 2 to adjust the pH to 4.3-4.7.
Reaction Step 2:
631.1 g of solution 2 (containing 0.253 mol of DAS disodium salt) were used. In total, 199.8 g of NaOH solution were added during this step.
Reaction Step 3:
In total, 178.3 g of NaOH solution were added during this step.

The resulting yellowish FWA solution had an $E_{1/1}$ value of 57.

HPLC analysis gave the following results: the main component according to the general formula (10) with n=1, $R_x$ and $R_y$=$CH_2CH_2OH$ and M=$Na^+$ was detected with 66.6%. The FWA according to the general formula (1) with n=1, $R_1$ to $R_8$=$CH_2CH_2OH$ and M=$Na^+$ was detected with 20.1%.

Preparation Example 4:

Reaction Steps 1 and 2 of the procedure as described in preparation example 1 were repeated. In reaction step 3, diisopropanolamine was used instead of diethanolamine.

Reaction Step 3:
102.0 g of an aqueous solution of diisopropanolamine, having an active content of 84.9 weight-%, were added to the reaction mixture with constant speed during 12 minutes. The temperature was then raised to 100° C. during 45 minutes. The reaction started at approx. 75° C., this lead to a drop of pH. When the pH value had reached 8.0, the addition of a NaOH solution with 10.4% strength was started and the pH was maintained at 8.0 through addition of this solution. After reaching 100° C., stirring was continued for further 3 hours while the pH was still maintained at 8.0. In total, 176.3 g NaOH solution were added during this step. The resulting FWA solution was then cooled to $_{55}$° C., filtered through a fluted paper filter, and allowed to cool furthermore down to 25° C.

The resulting yellowish FWA solution had an $E_{1/1}$ value of 53.

HPLC analysis gave the following results: the main component appearing as 3 peaks (different isomers) according to the general formula (10) with n=1, $R_x$ and $R_y$=$[CH_2CH(CH_3)OH]$ and M=$Na^+$ was detected with 90.2%. The FWA according to the general formula (1) with n=1, $R_1$ to $R_8$=$[CH_2CH(CH_3)OH]$ and M=$Na^+$ was detected with 3.6%.

Preparation Example 5

2875 g of an FWA solution obtained according to preparation example 2 were mixed at room temperature with 1711 g of demineralized water. The resulting solution was then concentrated and partially desalted in a membrane filtration process at 25° C. with a pressure of 40 bar. 1094 g of concentrated product having an $E_{1/1}$ value of 140.1 were thus obtained.

100 g of this concentrated product were mixed for 15 minutes on as magnetic stirrer at ambient temperature with 15 g of softened water and 30 g of the polyvinyl alcohol solution Polyviol® LL 2850 (from Wacker), having a strength of 25 weight-%. A formulation with an $E_{1/1}$ value of 97 and a polyvinyl alcohol content of 5.2 weight-% was obtained.

Preparation Example 6

100 g of the concentrated product as described in preparation example 5 above were first mixed for 5 minutes on as magnetic stirrer at ambient temperature with 30 g of softened water, then 15 g of melted polyethylene glycol 1550 in liquid form, having a temperature of 60° C., were added. Mixing was continued for another 15 minutes. A formulation with an $E_{1/1}$ value of 97 and a polyethylene glycol content of 10.3 weight-% was obtained.

Application Examples

Coating Application:
A paper coating color was prepared from the following raw materials:
945 g of the GCC powder Hydrocarb® 90 (from Omya)
405 g of the kaolin "Kaolin KN 83 Granulat" (kaolin content 99%, from Amberger Kaolinwerke)
8.5 g of the dispersant Polysalz® S (approx. 40% solids, from BASF)
270 g of the binder Litex® P 7110 (styrene-butadiene latex with approx. 50% solids, from Synthomer)
40 g of the polyvinyl alcohol solution Polyviol® LL 2850 having 25% solids (from Wacker)

100 g of an aqueous solution of the carboxymethyl cellulose Walocel® CRT 10 G (from Dow Wolff Cellulosics) having 10% solids
640.2 g of demineralized water
6.5 g of aqueous sodium hydroxide solution with a strength of 5%

For preparing the coating color, the above mentioned materials were mixed in the following manner using the given amounts:
Polysalz® S was first stirred into demineralized water at ambient temperature. To this mixture, GCC and kaolin were added and mixed in with a dissolver plate at 500 rpm for 5 minutes. Then the mixture was dispersed with an Ultra-Turrax device at 7000 rpm for 2 minutes. After this, the binder, the polyvinyl alcohol solution and the carboxymethyl cellulose solution were added subsequently under stirring. The pH of the coating color was adjusted to the range 8.4-8.6 by adding the aqueous sodium hydroxide solution.

Stirring was continued for another 5 minutes. A paper coating color with a solids content of 62.2% and a pigment content of 55.7% was obtained.

The coating color was separated into 19 portions of 100 g. The liquid FWA's according to the preparation examples 1-6 were diluted prior to the addition to an $E_{1/1}$ value of 50 by adding demineralized water. The FWA preparations were then added to the coating color samples in amounts of 0.37 g/0.75 g/1.12 g and stirred in for 5 minutes. For comparison purposes, the coating color without addition of FWA was applied in the same manner as described below:

The coating color samples were each applied to wood-free base paper sheets having a basis weight of approx. 83 g/m². For this purpose, the laboratory coater Erichsen K-Control-Coater, model K 202, was used.

The coated papers were then dried on a drum dryer at 95° C. for 1 minute and afterwards stored for 4 hours at 23° C. and a relative humidity of 50%. The applied coat weight was in the range of 14-16 g/m².

Then, CIE whiteness and ISO brightness values were determined by using a Datacolor ELREPHO SF 450 device.
The obtained results are shown in Table 1 below.

TABLE 1

| FWA amount (% related to dry matter in the coating colour) | FWA from preparation example No. | ISO brightness (%) | CIE whiteness |
|---|---|---|---|
| no FWA used | no FWA used | 81.0 | 66.9 |
| 0.59 | 1 | 86.9 | 87.3 |
| 1.21 | 1 | 89.7 | 95.9 |
| 1.80 | 1 | 91.3 | 100.6 |
| 0.59 | 2 | 87.1 | 88.3 |
| 1.21 | 2 | 89.9 | 97.0 |
| 1.80 | 2 | 91.6 | 101.6 |
| 0.59 | 3 | 87.3 | 88.4 |
| 1.21 | 3 | 90.1 | 97.4 |
| 1.80 | 3 | 91.9 | 102.2 |
| 0.59 | 4 | 86.8 | 87.1 |
| 1.21 | 4 | 89.8 | 96.5 |
| 1.80 | 4 | 91.3 | 100.9 |
| 0.59 | 5 | 87.1 | 88.4 |
| 1.21 | 5 | 90.3 | 98.0 |
| 1.80 | 5 | 91.9 | 102.3 |
| 0.59 | 6 | 87.2 | 88.3 |
| 1.21 | 6 | 90.2 | 97.6 |
| 1.80 | 6 | 91.9 | 102.4 |

It can be clearly seen that all tested FWA's lead to a significant increase of whiteness and brightness, when applied in a paper coating color.

Size Press Application:

The liquid FWA's according to the preparation examples 1 and 2 were first diluted to an $E_{1/1}$ value of 50 by adding demineralized water. Size press liquors with these FWA solutions were then prepared as follows: 1.67 g/3.33 g/5.00 g, respectively, of each FWA solution were blended at room temperature with 192.3 g of an aqueous solution of the starch Perfectamyl® A 4692 (from AVEBE) having a strength of 6.5 weight-%, then filled up to 250.0 g with demineralized water, and finally stirred for 5 minutes on a magnetic stirrer.

An unsized, woodfree paper with a basis weight of 107 g/m² was used for the surface sizing trials. The size press liquors were applied with a laboratory size press (from the company Mathis, type HF) using a speed of 2.5 m/min and a pressure of 2.5 bar.

Weighing the paper directly before and after the size press treatment yielded a wet pickup of the paper of approx. 90% for all treatment liquors.

For comparison purposes, the base paper was treated in an analogous manner without addition of an FWA to the size press liquor.

The treated papers were dried in each case on a drying cylinder for 2 minutes at 105° C., and afterwards stored in norm climate (23° C., 50° relative humidity) for 24 hours. Then, the ISO brightness and CIE whiteness values were determined using a Datacolor Elrepho SF 450 device.

The obtained results are summarized in the following Table 2.

TABLE 2

| FWA amount (% related to size press liquor) | FWA from preparation example No. | ISO brightness (%) | CIE whiteness |
|---|---|---|---|
| no FWA used | no FWA used | 85.1 | 80.4 |
| 0.67 | 1 | 103.9 | 136.7 |
| 1.33 | 1 | 107.2 | 144.9 |
| 2.0 | 1 | 109.2 | 148.8 |
| 0.67 | 2 | 105.0 | 138.9 |
| 1.33 | 2 | 108.2 | 145.7 |
| 2.0 | 2 | 109.6 | 148.1 |

It can be seen from the obtained results that the tested FWAs lead to a significant increase of whiteness and brightness, when applied to the paper surface in a size press application.

Wet End Application

Handsheets containing the FWA's from preparation example 1 and 2 were prepared as follows: an aqueous pulp suspension, containing 70 parts by weight of short-fiber chemical pulp and 30 parts by weight of long-fiber chemical pulp and having a freeness of 35° SR and a consistency of 0.625 weight-% was used to prepare the handsheets. The liquid FWAs from example 1 and 2 were diluted prior to the handsheet preparation to an $E_{1/1}$ value of 0.50 by adding demineralized water.

For each handsheet, 800 ml of the pulp suspension were placed in a beaker and stirred by means of a magnetic stirrer. From each diluted FWA solution, 3.0 g/6.0 g/9.0 g, respectively, were added. The pulp suspension was then allowed to stir for 10 minutes.

A handsheet former was then used to prepare handsheets of approx. 5 g dry weight and a basis weight of approx. 120 g/m². In each case, a wet filter paper was placed on the wire of the sheet former, then the pulp suspension was poured onto the wire and the water was removed by a suction pump. A second filter paper was used to cover the wet handsheet.

Then the handsheet was pressed and finally dried on a drying cylinder for 2 minutes at 105° C. The handsheets were afterwards stored in norm climate (23° C., 50% relative humidity) for 24 hours. Then, the ISO brightness and CIE whiteness values were determined using a Datacolor Elrepho SF 450 device.

For comparison purposes, a handsheet without addition of FWA was prepared and evaluated in an analogous manner.

The obtained results are summarized in the following Table 3.

TABLE 3

| Amount of diluted FWA solution; E1/1 value 0.50 (g) | FWA from preparation example No. | ISO brightness (%) | CIE whiteness |
|---|---|---|---|
| no FWA used | no FWA used | 81.6 | 65.4 |
| 3.0 | 1 | 97.7 | 116.8 |
| 6.0 | 1 | 101.6 | 127.3 |
| 9.0 | 1 | 103.7 | 132.1 |
| 3.0 | 2 | 99.3 | 120.5 |
| 6.0 | 2 | 102.4 | 128.0 |
| 9.0 | 2 | 103.3 | 130.1 |

It can be seen from the obtained results that the tested FWA's lead to a significant increase of whiteness and brightness, when applied to papermaking pulp prior to sheet formation (wet end application).

The invention claimed is:

1. A compound having the following formula (1):

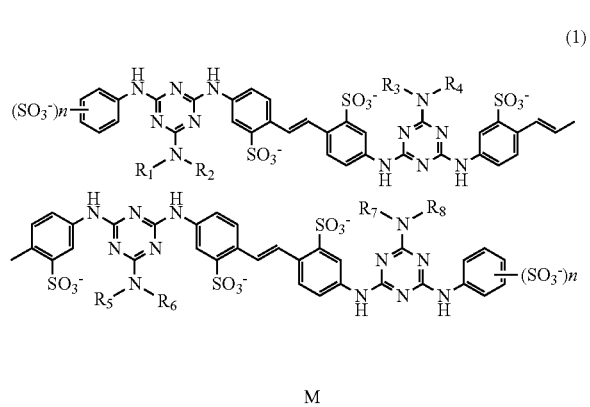

wherein n is 0, 1, or 2; and wherein $R_1$, $R_2$, $R_3$, $R_4$, $R_5$, $R_6$, $R_7$ and $R_8$ independently of each other are H, linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, phenyl substituted with $SO_3^-$, —$(CH_2)_i$—$SO_3^-$, —$(CH_2)_i$-phenyl, —$(CH_2)_k$—COOM, —$(CH_2)_k$—COOR$_9$, —$(CH_2)_k$—CONH$_2$, —$(CH_2)_k$—OR$_9$, wherein i is an integer from 1 to 3, k is an integer from 1 to 4, and $R_9$ is linear or branched $C_1$-$C_3$ alkyl; or $R_1$ and $R_2$, or $R_3$ and $R_4$, or $R_5$ and $R_6$, or $R_7$ and $R_8$ independently of each other together with the nitrogen atom form a morpholine, a piperidine or a pyrrolidine ring; and wherein M represents the corresponding cationic charge equivalent selected from the cations $H^+$, alkali metal cation, $Ca^{2+}$, $Mg^{2+}$, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2, and o≠p, alkyl is linear or branched; and mixtures of said cations.

2. The compound of claim 1, wherein n is an integer of 1 or 2; the substituent —$NR_1R_2$ is identical to —$NR_7R_8$, the substituent —$NR_3R_4$ is identical to —$NR_5R_6$; and M is selected from the cations $H^+$, $Na^+$, $Li^+$, $K^+$, ammonium, ammonium which is mono-, di-, tri- or tetra-substituted by $C_2$-$C_3$ hydroxyalkyl radicals, or mixtures of said cations.

3. The compound of claim 1, wherein n is an integer of 1 or 2; the substituents $R_1$ to $R_8$ are selected from H, linear or branched $C_1$-$C_4$ alkyl, linear or branched $C_2$-$C_4$ hydroxyalkyl, —$(CH_2)_i$—$SO_3^+$, wherein i is an integer from 1 to 3, and phenyl substituted with $SO_3^-$; and M is selected from the cations $H^+$, $Na^+$, $Li^+$, $K^+$, ammonium, ammonium which is mono-, di-, tri- or tetra-substituted by $C_2$-$C_3$ hydroxyalkyl radicals, or mixtures of said cations.

4. The compounds of claim 1, wherein $R_1$ to $R_8$ independently of each other are selected from H, linear or branched $C_1$-$C_3$ alkyl, linear or branched $C_2$-$C_3$ hydroxyalkyl, phenyl substituted with $SO_3^-$, and —$CH_2$—$CH_2$—$SO_3^-$.

5. A process for preparing a compound of formula (1) according to claim 1, wherein the process comprises the following steps:
in a first reaction step, 2,4,6-trichloro-1,3,5-triazine (cyanuric chloride) is reacted with an aromatic amine of the formula (2) and a compound of formula (3) according to the following reaction scheme, to obtain a mixture of the compounds of formula (5) and formula (6):

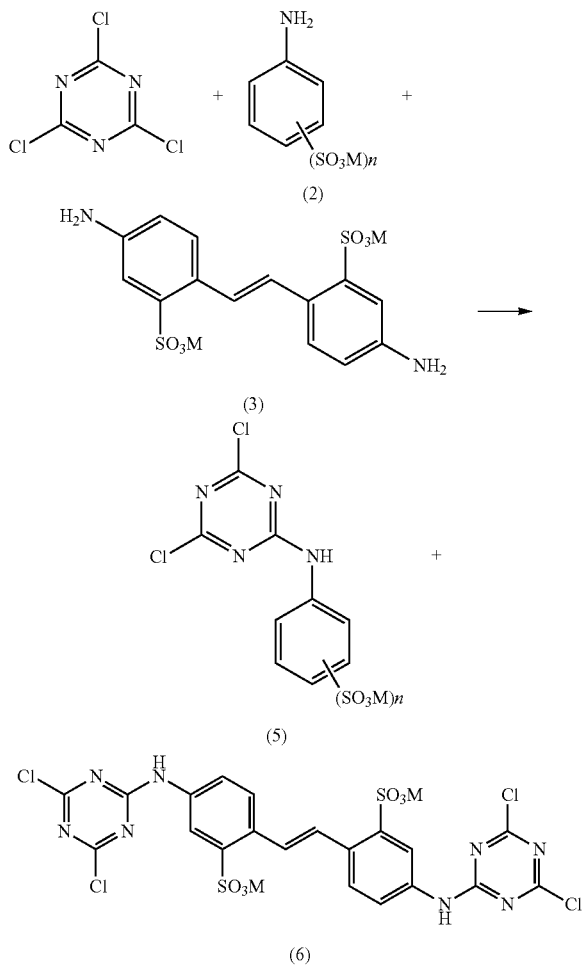

wherein n is 0, 1, or 2; and wherein M represents the corresponding cationic charge equivalent selected from the cations H⁺, alkali metal cation, $Ca^{2+}$, $Mg^{2+}$, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2, and o≠p, alkyl is linear or branched; and mixtures of said cations;

in a second reaction step, the obtained mixture of the compounds of formulae (5) and (6) is reacted with a compound of formula (3) according to the following reaction scheme, to obtain a mixture of the compounds of formula (7) and formula (8):

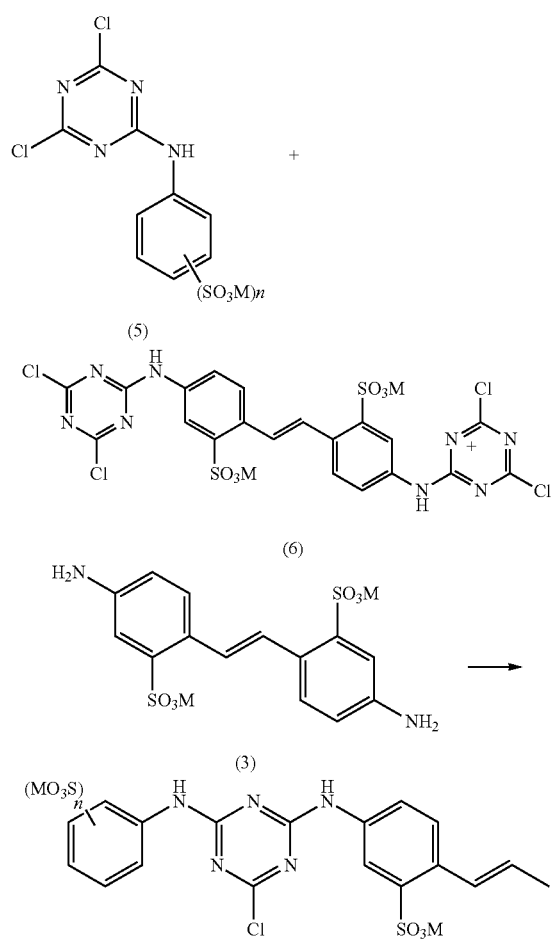

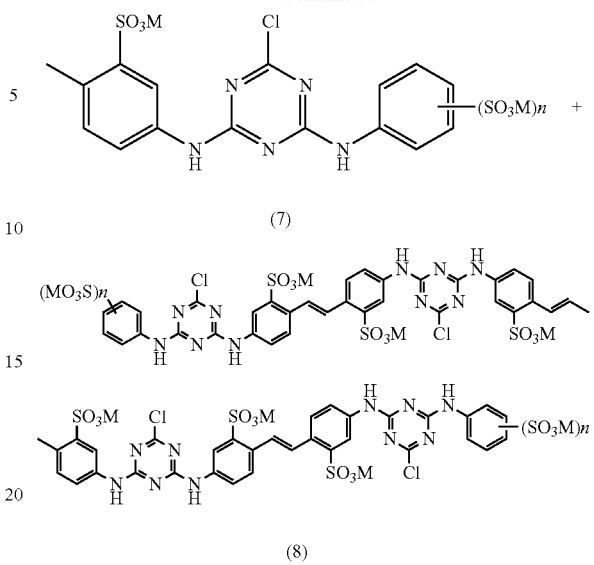

wherein n is 0, 1 or 2; and M represents the corresponding cationic charge equivalent selected from the cations H⁺, alkali metal cation, $Ca^{2+}$, $Mg^{2+}$, ammonium, $C_1$-$C_4$ tetraalkyl ammonium, ammonium which is mono-, di-, tri- or tetra-sibstituted by $C_2$-$C_3$, hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2, and o≠p, alkyl is linear or branched, and mixtures of said cations;

in a third reaction step the obtained mixture of the compounds of formulae (7) and (8) is reacted with at least one amine selected from ammonia, primary and secondary amines, wherein the organic substituents of the primary and secondary amine are selected from linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, phenyl substituted with $SO_3^-$, —$(CH_2)_i$—$SO_3^-$, —$(CH_2)_i$-phenyl, —$(CH_2)_k$—COOM, —$(CH_2)_k$—$COOR_9$, —$(CH_2)_k$—$CONH_2$, —$(CH_2)_k$—$OR_9$, wherein i is an integer from 1 to 3, k is an integer from 1 to 4, and $R_9$ is linear or branched $C_1$-$C_3$ alkyl;

or the substituents of the secondary amine together with the nitrogen atom form a morpholine, a piperidine or a pyrrolidine ring,

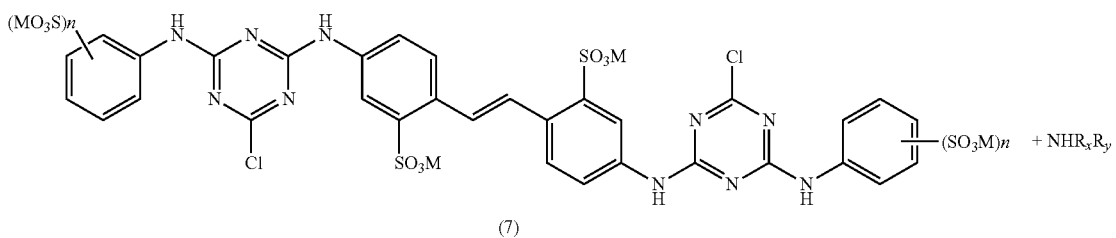

-continued

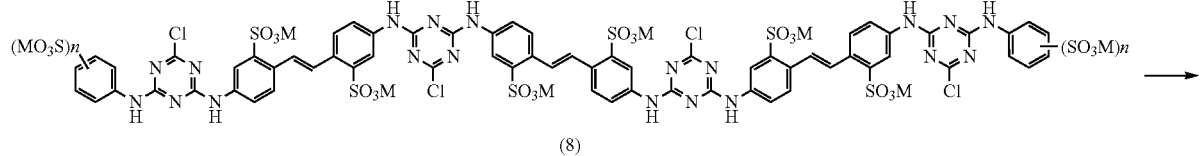

(8)

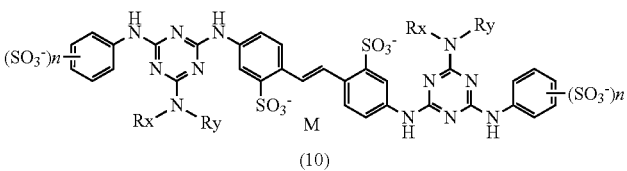

(10)

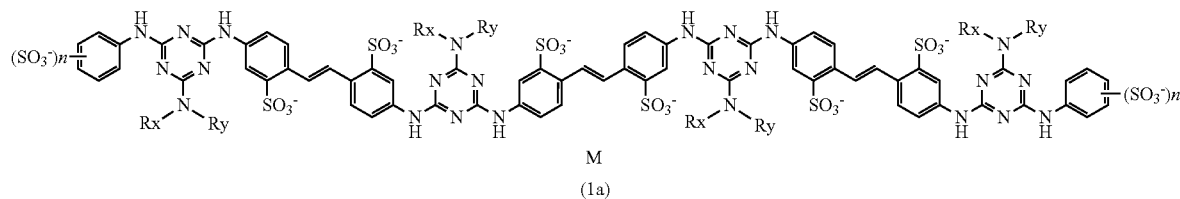

(1a)

6. The process of claim 5, wherein, in the first reaction step, the molar ratio of cyanuric chloride to the compound of formula (2) to the compound of formula (3) is in the range of from 1:0.65 to 1.095:0.0025 to 0.15.

7. The process of claim 5, wherein in the first reaction step, the molar ratio of cyanuric chloride to the compound of formula (2) to the compound of formula (3) is in the range of from 1:0.70 to 0.80:0.10 to 0.15.

8. The process of claim 5, wherein in the first reaction step, the molar ratio of cyanuric chloride to the compound of formula (2) to the compound of formula (3) is in the range of from 1:0.80 to 1:08:0.01 to 0.075.

9. The process of claim 5, wherein in the second reaction step, the molar ratio of cyanuric chloride to the compound of formula (3) is in the range of from 1:0.425 to 0.525.

10. The process of claim 5, wherein in the second reaction step, the molar ratio of cyanuric chloride to the compound of formula (3) is in the range of from 1:0.425 to 0.500.

11. The process of claim 5, wherein in the third reaction step, the molar ratio of cyanuric chloride to the total amount of amines is in the range of from 1:1.00 to 1.50.

12. The process of claim 5, wherein in the third reaction step, the molar ratio of cyanuric chloride to the total amount of amines is in the range of from 1:1.00 to 1.25.

13. The process of claim 5, wherein a compound (1a) is prepared, wherein the process comprises the first and second reaction steps of the preparation of the compound of formula (1), and wherein in the third reaction step, the obtained mixture of the compounds of formulae (7) and (8) is reacted with an amine of the formula $NHR_xR_y$, to obtain a mixture of the compound of formula (1a) and the compound of formula (10):

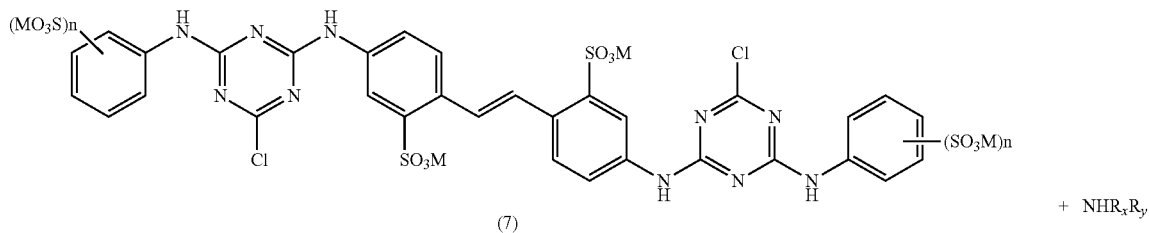

(7)

+ $NHR_xR_y$

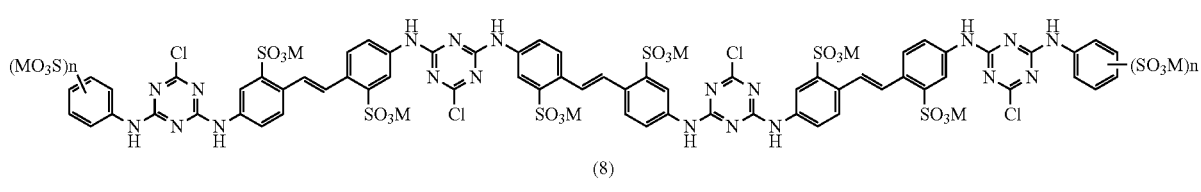

(8)

→

-continued

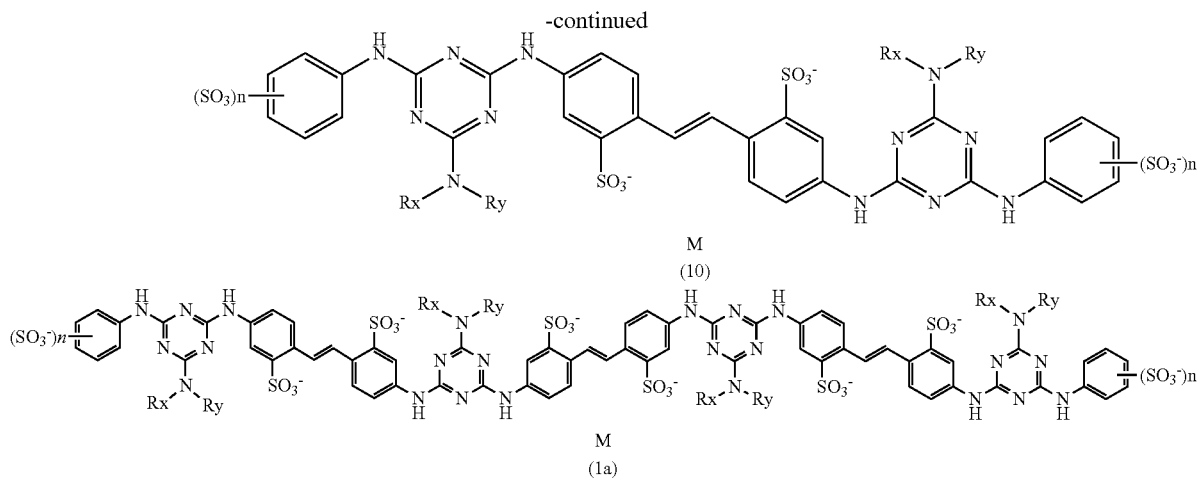

wherein n is 0, 1, or 2; and M represents the corresponding cationic charge equivalent selected from the cations H$^+$, alkali metal cation, Ca$^{2+}$, Mg$^{2+}$, ammonium, C$_1$-C$_4$ tetraalkyl ammonium, ammonium which is mono-, di-, tri- or tetra-substituted by C$_2$-C$_3$ hydroxyalkyl radicals, and NH(R$_{10}$)$_o$(R$_{11}$)$_p^+$ with R$_{10}$ being C$_1$-C$_4$ alkyl and R$_{11}$ being C$_2$-C$_3$ hydroxyalkyl, wherein both o and p are an integer of 1 or 2, and o≠p, alkyl is linear or branched; and mixtures of said cations, and wherein R$_x$ and R$_y$ independently of each other are H, linear or branched C$_1$-C$_4$ alkyl, linear or branched C$_2$-C$_4$ hydroxyalkyl, linear or branched C$_1$-C$_4$ alkoxyalkyl, linear or branched C$_2$-C$_4$ cyanoalkyl, or —(CH$_2$)$_i$—SO$_3^-$, —(CH$_2$)$_i$-phenyl, —(CH$_2$)$_k$—COOM, —(CH$_2$)$_k$—COOR$_9$, —(CH$_2$)$_k$—CONH$_2$, —(CH$_2$)$_k$—OR$_9$, wherein i is an integer from 1 to 3 and wherein k is an integer from 1 to 4, R$_9$ is linear or branched C$_1$-C$_3$ alkyl, or R$_x$ and R$_y$ independently of each other together with the nitrogen atom form a morpholine, a piperidine or a pyrrolidine ring.

14. A composition comprising
at least one compound of formula (1)

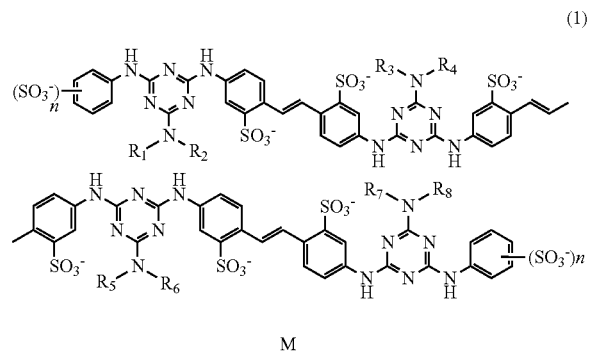

wherein n is 0, 1, or 2; and wherein R$_1$, R$_2$, R$_3$, R$_4$, R$_5$, R$_6$, R$_7$ and R$_8$ independently of each other are H, linear or branched C$_1$-C$_4$ alkyl, linear or branched C$_2$-C$_4$ hydroxyalkyl, linear or branched C$_1$-C$_4$ alkoxyalkyl, linear or branched C$_2$-C$_4$ cyanoalkyl, phenyl substituted with SO$_3^-$, —(CH$_2$)$_i$—SO$_3^-$, —(CH$_2$)$_i$-phenyl, —(CH$_2$)$_k$—COOM, —(CH$_2$)$_k$—COOR$_9$, —(CH$_2$)$_k$—CONH$_2$, —(CH$_2$)$_k$—OR$_9$, wherein i is an integer from 1 to 3, k is an integer from 1 to 4, and R$_9$ is linear or branched C$_1$-C$_3$ alkyl; or R$_1$ and R$_2$, or R$_3$ and R$_4$, or R$_5$ and R$_6$, or R$_7$ and R$_8$ independently of each other together with the nitrogen atom form a morpholine, a piperidine or a pyrrolidine ring; and wherein M represents the corresponding cationic charge equivalent selected from the cations H$^+$, alkali metal cation, Ca$^{2+}$, Mg$^{2+}$, ammonium, C$_1$-C$_4$ tetraalkyl ammonium, ammonium which is mono-, di-, tri- or tetra-substituted by C$_2$-C$_3$ hydroxyalkyl radicals, and NH(R$_{10}$)$_o$(R$_{11}$)$_p^+$ with R$_{10}$ being C$_1$-C$_4$ alkyl and R$_{11}$ being C$_2$-C$_3$ hydroxyalkyl, wherein both o and p are an integer of 1 or 2, and o≠p, alkyl is linear or branched; and mixtures of said cations: and at least one further fluorescent whitening agent (FWA) selected from the compound of formula (4) and the compound of formula (9):

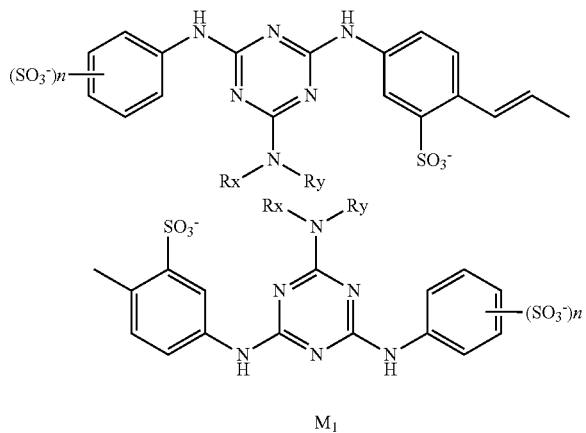

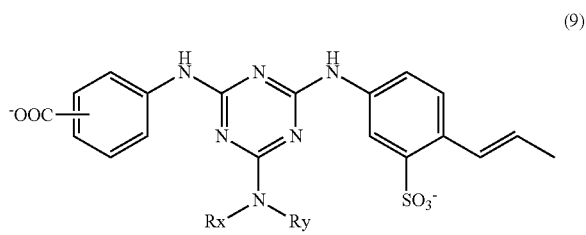

-continued

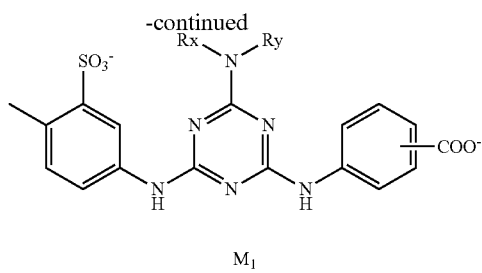

M₁ wherein n=0, 1, or 2, $R_x$ and $R_y$ independently of each other are H, $C_1$-$C_4$ alkyl, $C_2$-$C_4$ hydroxyalkyl, $C_1$-$C_4$ alkoxyalkyl, $C_2$-$C_4$ cyanoalkyl, wherein the alkyl residue is linear or branched, or —$(CH_2)_i$—$SO_3^-$, —$(CH_2)_i$-phenyl, —$(CH_2)_k$—COOM₁, —$(CH_2)_k$—$COOR_9$, —$(CH_2)_k$—$CONH_2$, —$(CH_2)_k$—$OR_9$, wherein i is an integer from 1 to 3 and wherein k is an integer from 1 to 4, $R_9$ is linear or branched $C_1$-$C_3$ alkyl, or $R_x$ and $R_y$ independently of each other together with the nitrogen atom form a morpholine, a piperidine or a pyrrolidine ring; and wherein M₁ represents the corresponding cationic charge equivalent selected from the cations H⁺, alkali metal cation, $Ca^{2+}$, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2 and o≠p, and alkyl is linear or branched; and mixtures of said cations.

15. The composition of claim 14, wherein the compound of formula (1) is the compound of formula (1a):

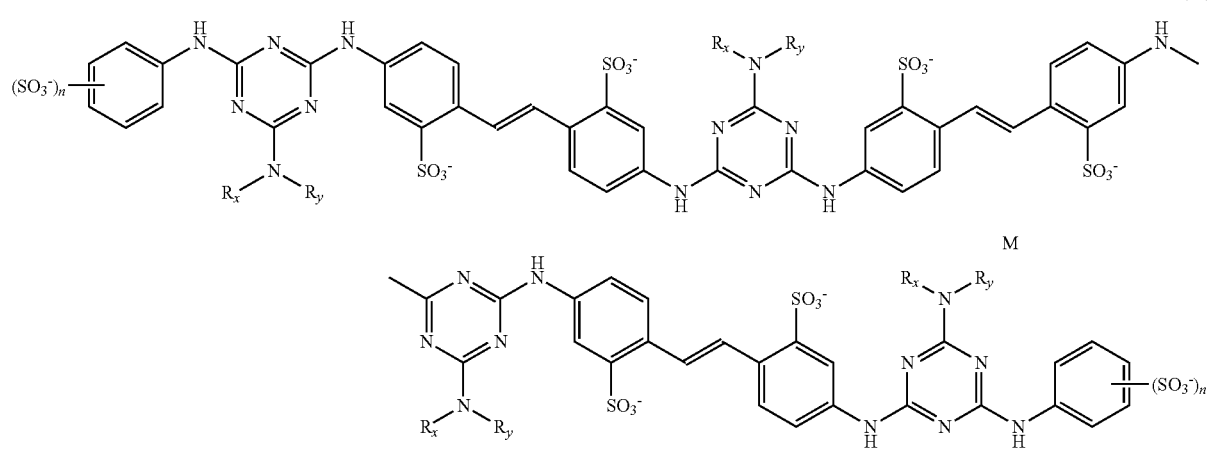

wherein n is 0, 1, or 2; and M represents the corresponding cationic charge equivalent selected from the cations H⁺, alkali metal cation, $Ca^{2+}$, $Mg^{2+}$, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2 and o≠p alkyl is linear or branched; and mixtures of said cations, and wherein $R_x$ and $R_y$ independently of each other are H, linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, or —$(CH_2)_i$—$SO_3^-$, —$(CH_2)_i$-phenyl, —$(CH_2)_k$—COOM₁, —$(CH_2)_k$—$COOR_9$, —$(CH_2)_k$—$CONH_2$, —$(CH_2)_k$—$OR_9$, wherein i is an integer from 1 to 3 and wherein k is an integer from 1 to 4, $R_9$ is linear or branched $C_1$-$C_3$ alkyl, or $R_x$ and $R_y$ independently of each other together with the nitrogen atom form a morpholine, a piperidine or a pyrrolidine ring.

16. The composition of claim 14, wherein the compound of formula (1) is present in an amount of 1 to 90 weight-%, and the at least one further fluorescent whitening agent (FWA) is present in an amount of 10 to 99 weight %, in each case based on the total amount of the compounds of formula (1) and the further fluorescent whitening agent (FWA).

17. A coating color comprising
at least one white pigment;
at least one binder; and
at least one compound of formula (1):

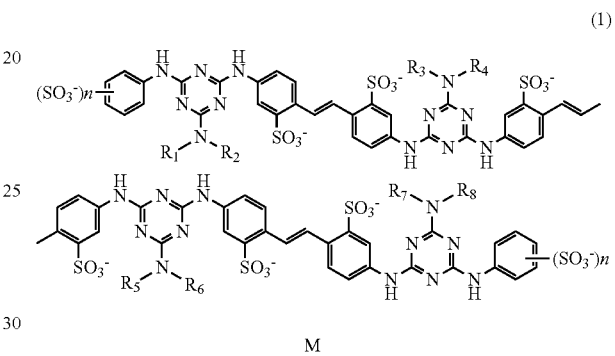
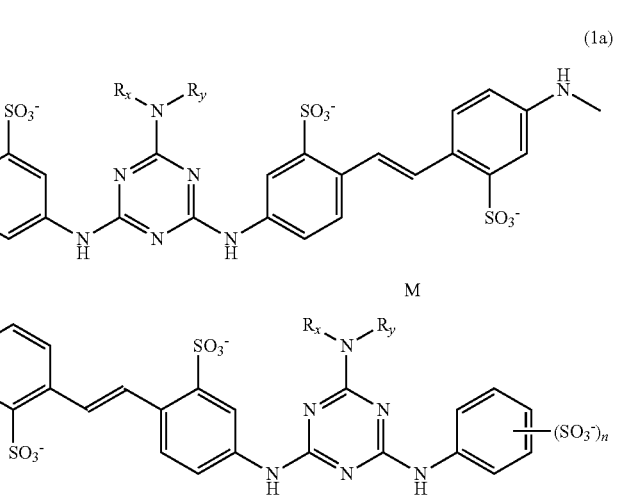

M wherein n is 0, 1, or 2; and wherein $R_1$, $R_2$, $R_3$, $R_4$, $R_5$, $R_6$, $R_7$ and $R_8$ independently of each other are H, linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, phenyl substituted with $SO_3^-$, —$(CH_2)_i$—$SO_3^-$, —$(CH_2)_i$-phenyl, —$(CH_2)_k$—COOM, —$(CH_2)_k$—$COOR_9$, —$(CH_2)_k$—$CONH_2$, —$(CH_2)_k$—$OR_9$, wherein i is an integer from 1 to 3, k is an integer from 1 to 4, and $R_9$ is linear or branched $C_1$-$C_3$ alkyl; or $R_1$ and $R_2$, or $R_3$ and $R_4$, or $R_5$ and $R_6$, or $R_7$ and $R_8$ independently of each other together with the nitrogen atom form a morpholine, a piperidine or a pyrrolidine ring; and wherein M represents the corresponding cationic charge equivalent selected from the cations H⁺, alkali metal cation, Ca²⁺, Mg²⁺, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2, and o≠p, alkyl is linear or branched; and mixtures of said cations, or a composition comprising the compound of formula (1) and at least one further fluorescent whitening agent (FWA) selected from the compound of formula (4) and the compound of formula (9):

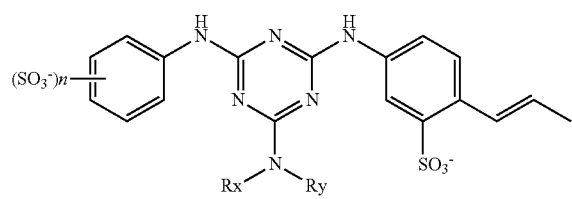

(4)

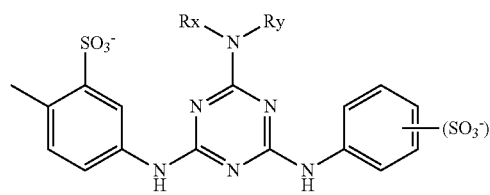

$M_1$

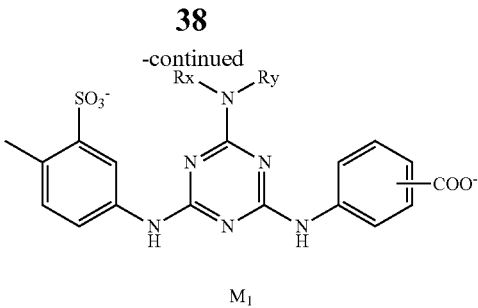

$M_1$ wherein n=0, 1, or 2, $R_x$ and $R_y$ independently of each other are H, $C_1$-$C_4$ alkyl, $C_2$-$C_4$ hydroxyalkyl, $C_1$-$C_4$ alkoxyalkyl, $C_2$-$C_4$ cyanoalkyl, wherein the alkyl residue is linear or branched, or —$(CH_2)_i$—$SO_3^-$, —$(CH_2)_i$-phenyl, —$(CH_2)_k$—$COOM_1$, —$(CH_2)_k$—$COOR_9$, —$(CH_2)_k$—$CONH_2$, —$(CH_2)_k$—$OR_9$, wherein i is an integer from 1 to 3 and wherein k is an integer from 1 to 4, $R_9$ is linear or branched $C_1$-$C_3$ alkyl, or $R_x$ and $R_y$ independently of each other together with the nitrogen atom form a morpholine, a piperidine or a pyrrolidine ring; and wherein $M_1$ represents the corresponding cationic charge equivalent selected from the cations H⁺, alkali metal cation, Ca²⁺, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2 and o≠p, and alkyl is linear or branched; and mixtures of said cations.

18. The coating color of claim 17, wherein said composition comprises the compound of formula (1a):

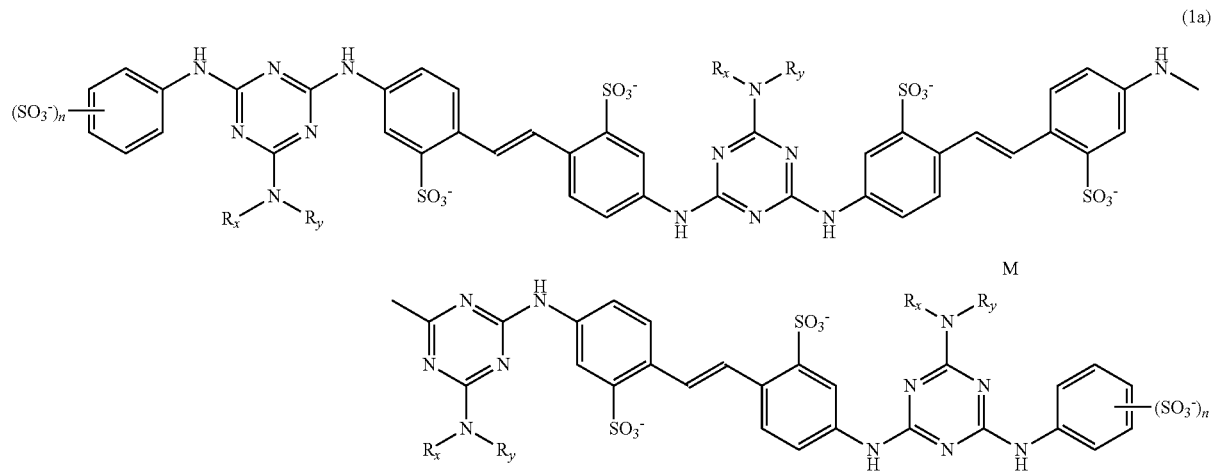

(1a)

M

-continued

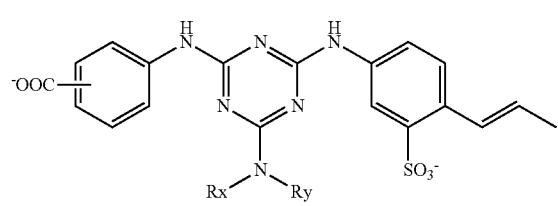

(9)

wherein n is 0, 1, or 2; and M represents the corresponding cationic charge equivalent selected from the cations H⁺, alkali metal cation, Ca²⁺, Mg²⁺, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with R being $C_1$-$C_4$ alkyl and $R_{11}$ being $C_2$-$C_3$ hydroxyalkyl, wherein both o and p are an integer of 1 or 2, and o≠p, alkyl is linear or branched; and mixtures of said cations, and wherein $R_x$ and $R_y$ independently of each other are H, linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, or —$(CH_2)_i$—$SO_3^-$, —$(CH_2)_i$-phenyl, —$(CH_2)_k$—COOM, —$(CH_2)_k$—COOR$_9$, —$(CH_2)_k$—CONH$_2$, —$(CH_2)_k$—OR$_9$, wherein i is an integer from 1 to 3 and wherein k is an integer from 1 to 4, $R_9$ is linear or branched $C_1$-$C_3$ alkyl, or $R_x$ and $R_y$ independently of each other together with the nitrogen atom form a morpholine, a piperidine or a pyrrolidine ring.

19. A size press or film press liquor comprising:
at least one sizing agent; and
at least one compound of formula (1):

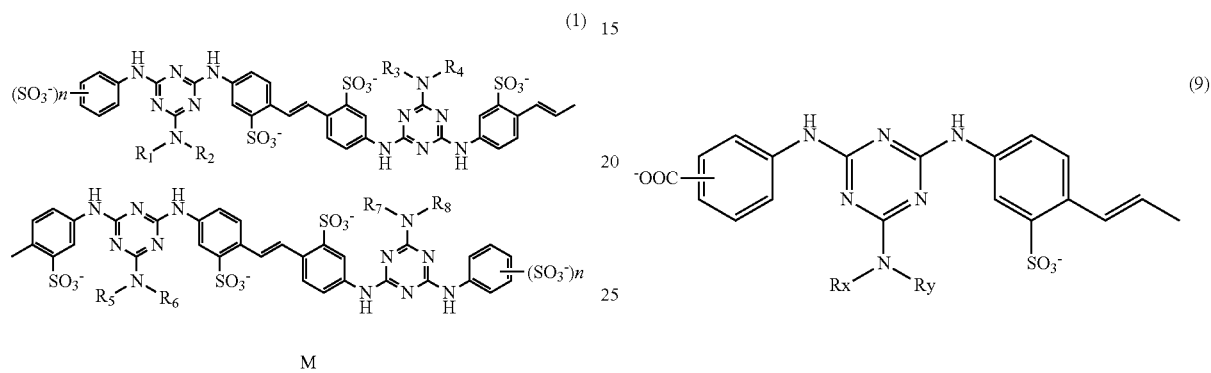

wherein n is 0, 1, or 2; and wherein $R_1$, $R_2$, $R_3$, $R_4$, $R_5$, $R_6$, $R_7$ and $R_8$ independently of each other are H, linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, phenyl substituted with $SO_3^-$, —$(CH_2)_i$—$SO_3^-$, —$(CH_2)_i$-phenyl, —$(CH_2)_k$—COOM, —$(CH_2)_k$—COOR$_9$, —$(CH_2)_k$—CONH$_2$, —$(CH_2)_k$—OR$_9$, wherein i is an integer from 1 to 3, k is an integer from 1 to 4, and $R_9$ is linear or branched $C_1$-$C_3$ alkyl; or $R_1$ and $R_2$, or $R_3$ and $R_4$, or $R_5$ and $R_6$, or $R_7$ and $R_8$ independently of each other together with the nitrogen atom form a morpholine, a piperidine or a pyrrolidine ring; and wherein M represents the corresponding cationic charge equivalent selected from the cations H$^+$, alkali metal cation, Ca$^{2+}$, Mg$^{2+}$, ammonium, $C_1$-$C_4$ tetraalkyl ammonium, ammonium which is mono-, di-, tri- or tetra-substituted by $C_2$-$C_3$ hydroxyalkyl radicals, and NH(R$_{10}$)$_o$(R$_{11}$)$_p^+$ with $R_{10}$ being $C_1$-$C_4$ alkyl and $R_{11}$ being $C_2$-$C_3$ hydroxyalkyl, wherein both o and p are an integer of 1 or 2, and o≠p, alkyl is linear or branched; and mixtures of said cations, or a composition comprising the compound of formula (1) and at least one further fluorescent whitening agent (FWA) selected from the compound of formula (4) and the compound of formula (9):

wherein n=0, 1, or 2, $R_x$ and $R_y$ independently of each other are H, $C_1$-$C_4$ alkyl, $C_2$-$C_4$ hydroxyalkyl, $C_1$-$C_4$ alkoxyalkyl, $C_2$-$C_4$ cyanoalkyl, wherein the alkyl residue is linear or branched, or —$(CH_2)_i$—$SO_3^-$, —$(CH_2)_i$-phenyl, —$(CH_2)_k$—COOM$_1$, —$(CH_2)_k$—COOR$_9$, —$(CH_2)_k$—CONH$_2$, —$(CH_2)_k$—OR$_9$, wherein i is an integer from 1 to 3 and wherein k is an integer from 1 to 4, $R_9$ is linear or branched $C_1$-$C_3$ alkyl, or $R_x$ and $R_y$ independently of each other together with the nitrogen atom form a morpholine, a piperidine or a pyrrolidine ring; and wherein M$_1$ represents the corresponding cationic charge equivalent selected from the cations H$^+$, alkali metal cation, Ca$^{2+}$, ammonium, $C_1$-$C_4$ tetraalkyl ammonium, ammonium which is mono-, di-, tri- or tetra-substituted by $C_2$-$C_3$ hydroxyalkyl radicals, and NH(R$_{10}$)$_o$(R$_{11}$)$_p^+$ with $R_{10}$ being $C_1$-$C_4$ alkyl and $R_{11}$ being $C_2$-$C_3$ hydroxyalkyl, wherein both o and p are an integer of 1 or 2 and o≠p, and alkyl is linear or branched; and mixtures of said cations.

20. The size press or film press liquor of claim 19, wherein said composition comprises the compound of formula (1a):

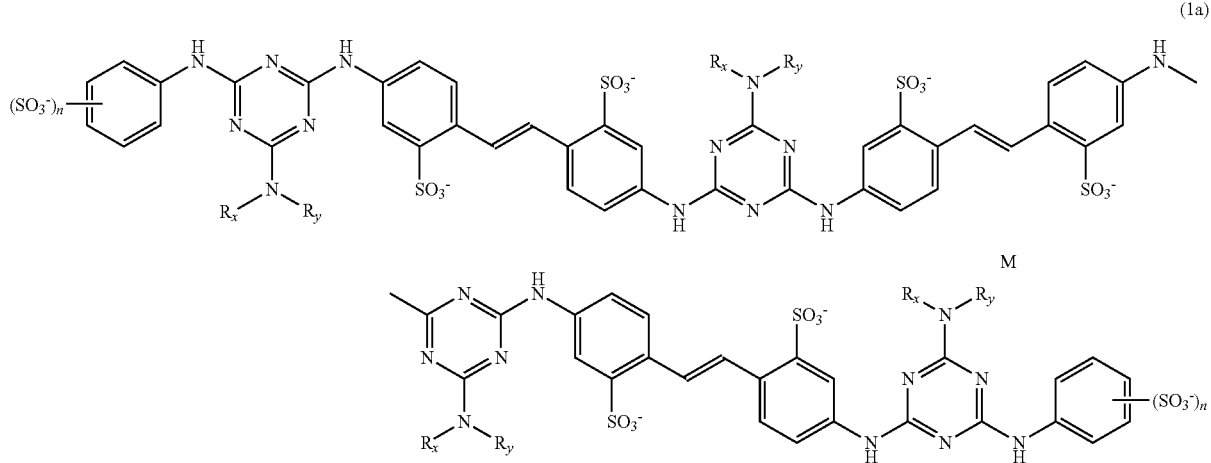

(1a)

wherein n is 0, 1, or 2; and M represents the corresponding cationic charge equivalent selected from the cations H⁺, alkali metal cation, $Ca^{2+}$, $Mg^{2+}$, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2, and o≠p, alkyl is linear or branched; and mixtures of said cations, and wherein $R_x$ and $R_y$ independently of each other are H, linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, or —$(CH_2)_i$—$SO_3^{31}$, —$(CH_2)_i$-phenyl, —$(CH_2)_k$—COOM, —$(CH_2)_k$—$COOR_9$, —$(CH_2)_k$—$CONH_2$, —$(CH_2)_k$—$OR_9$, wherein i is an integer from 1 to 3 and wherein k is an integer from 1 to 4, $R_9$ is linear or branched $C_1$-$C_3$ alkyl, or $R_x$ and $R_y$ independently of each other together with the nitrogen atom form a morpholine, a piperidine or a pyrrolidine ring.

21. A method for optically whitening cellulose-based materials comprising treating the cellulose-based material with at least one compound of formula (1):

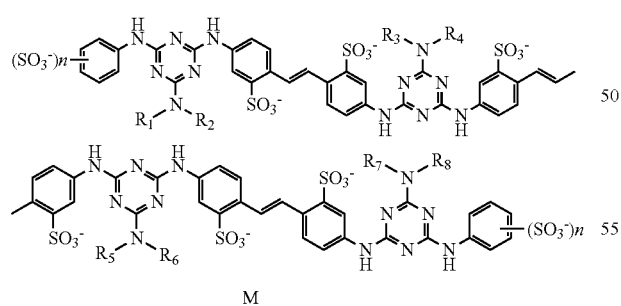

(1)

wherein n is 0, 1, or 2; and wherein $R_1$, $R_2$, $R_3$, $R_4$, $R_5$, $R_6$, $R_7$ and $R_8$ independently of each other are H, linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, phenyl substituted with $SO_3^-$, —$(CH_2)_i$—$SO_3^-$, —$(CH_2)_i$-phenyl, —$(CH_2)_k$—COOM, —$(CH_2)_k$—$COOR_9$, —$(CH_2)_k$—$CONH_2$, —$(CH_2)_k$—$OR_9$, wherein i is an integer from 1 to 3, k is an integer from 1 to 4, and $R_9$ is linear or branched $C_1$-$C_3$ alkyl; or $R_1$ and $R_2$, or $R_3$ and $R_4$, or $R_5$ and $R_6$, or $R_7$ and $R_8$ independently of each other together with the nitrogen atom form a morpholine, a piperidine or a pyrrolidine ring; and wherein M represents the corresponding cationic charge equivalent selected from the cations H⁺, alkali metal cation, $Ca^{2+}$, $Mg^{2+}$, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2, and o≠p, alkyl is linear or branched; and mixtures of said cations, or a composition comprising the compound of formula (1) and at least one further fluorescent whitening agent (FWA) selected from the compound of formula (4) and the compound of formula (9):

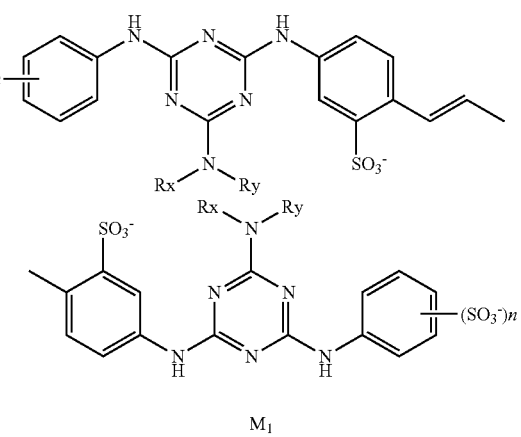

(4)

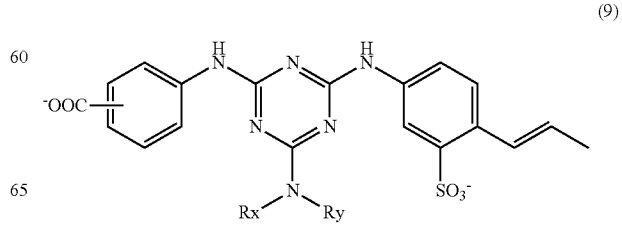

(9)

-continued

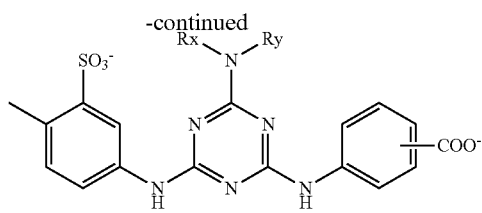

M₁ wherein n=0, 1, or 2, $R_x$ and $R_y$ independently of each other are H, $C_1$-$C_4$ alkyl, $C_2$-$C_4$ hydroxyalkyl, $C_1$-$C_4$ alkoxyalkyl, $C_2$-$C_4$ cyanoalkyl, wherein the alkyl residue is linear or branched, or —$(CH_2)_i$—$SO_3^-$, —$(CH_2)_i$-phenyl, —$(CH_2)_k$—$COOM_1$, —$(CH_2)_k$—$COOR_9$, —$(CH_2)_k$—$CONH_2$, —$(CH_2)_k$—$OR_9$, wherein i is an integer from 1 to 3 and wherein k is an integer from 1 to 4, $R_9$ is linear or branched $C_1$-$C_3$ alkyl, or $R_x$ and $R_y$ independently of each other together with the nitrogen atom form a morpholine, a piperidine or a pyrrolidine ring; and
  wherein $M_1$ represents the corresponding cationic charge equivalent selected from the cations H⁺, alkali metal cation, $Ca^{2+}$, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2 and o≠p, and alkyl is linear or branched; and mixtures of said cations.

22. The method of claim 21, wherein said composition comprises the compound of formula (1a):

—$(CH_2)_k$—$COOR_9$, —$(CH_2)_k$—$CONH_2$, —$(CH_2)_k$—$OR_9$, wherein i is an integer from 1 to 3 and wherein k is an integer from 1 to 4, $R_9$ is linear or branched $C_1$-$C_3$ alkyl, or $R_x$ and $R_y$ independently of each other together with the nitrogen atom form a morpholine, a piperidine or a pyrrolidine ring.

23. A cellulose-based material comprising at least one compound of formula (1):

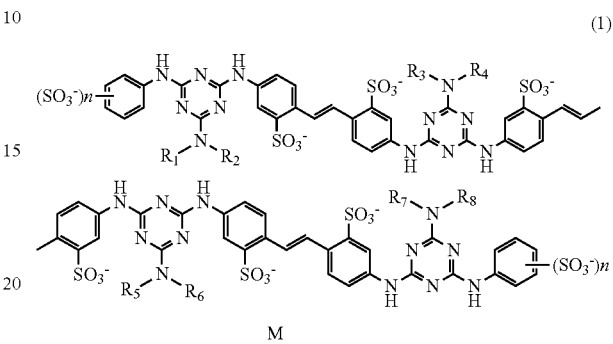

M (1)

wherein n is 0, 1, or 2; and wherein $R_1$, $R_2$, $R_3$, $R_4$, $R_5$, $R_6$, $R_7$ and $R_8$ independently of each other are H, linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, phenyl substituted with $SO_3^-$, —$(CH_2)_i$—$SO_3^-$, —$(CH_2)_i$-phenyl, —$(CH_2)_k$—COOM, —$(CH_2)_k$—$COOR_9$, —$(CH_2)_k$—$CONH_2$, —$(CH_2)_k$—$OR_9$, wherein i is an integer from 1 to 3, k is an integer from 1 to 4, and $R_9$ is linear or (1a)

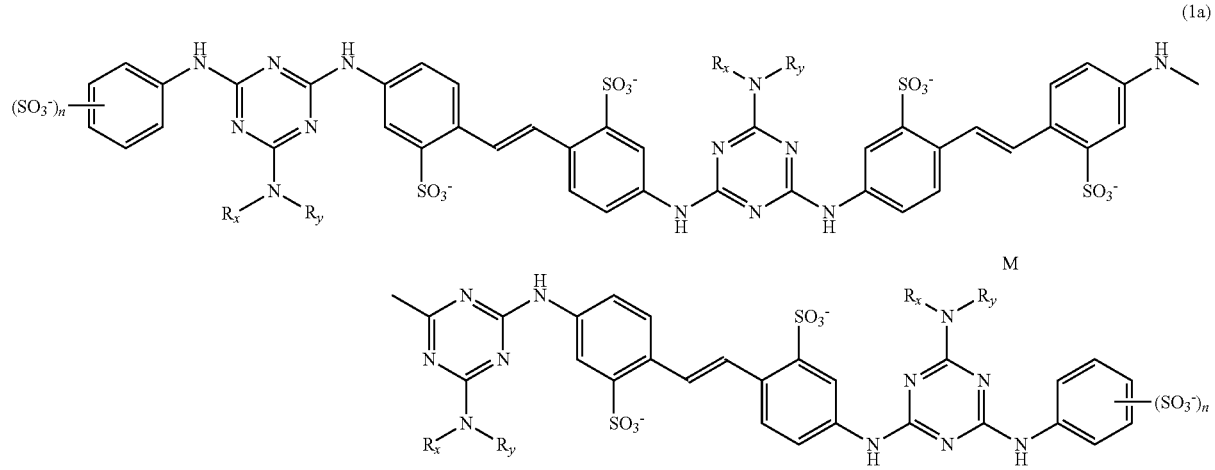

wherein n is 0, 1, or 2; and M represents the corresponding cationic charge equivalent selected from the cations H⁺, alkali metal cation, $Ca^{2+}$, $Mg^{2+}$, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2, and o≠p, alkyl is linear or branched; and mixtures of said cations, and wherein $R_x$ and $R_y$ independently of each other are H, linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, or —$(CH_2)_i$—$SO_3^-$, —$(CH_2)_i$-phenyl, —$(CH_2)_k$—COOM, branched $C_1$-$C_3$ alkyl; or $R_1$ and $R_2$, or $R_3$ and $R_4$, or $R_5$ and $R_6$, or $R_7$ and $R_8$ independently of each other together with the nitrogen atom form a morpholine, a piperidine or a pyrrolidine ring; and wherein M represents the corresponding cationic charge equivalent selected from the cations H⁺, alkali metal cation, $Ca^{2+}$, $Mg^{2+}$, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2, and o≠p, alkyl is linear or branched; and mixtures of said cations, or a composition comprising the compound of formula (1) and at least one further fluorescent whitening agent (FWA) selected from the compound of formula (4) and the compound of formula (9):

(4)

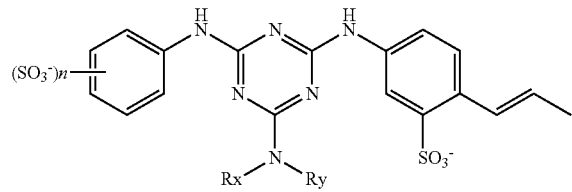

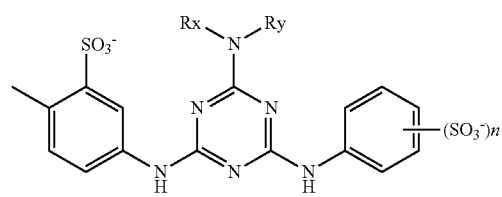

(9)

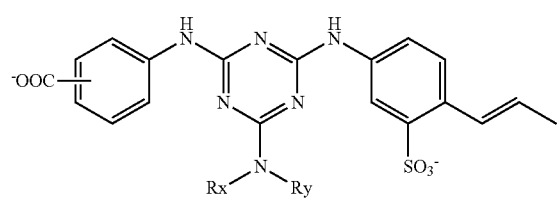

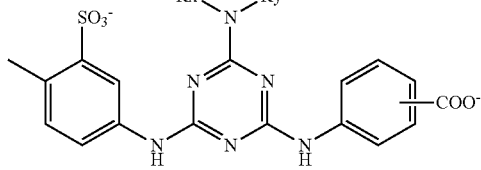

wherein n=0, 1, or 2, $R_x$ and $R_y$ independently of each other are H, $C_1$-$C_4$ alkyl, $C_2$-$C_4$ hydroxyalkyl, $C_1$-$C_4$ alkoxyalkyl, $C_2$-$C_4$ cyanoalkyl, wherein the alkyl residue is linear or branched, or —$(CH_2)_i$—$SO_3^-$, —$(CH_2)_i$-phenyl, —$(CH_2)_k$—$COOM_1$, —$(CH_2)_k$—$COOR_9$, —$(CH_2)_k$—$CONH_2$, —$(CH_2)_k$—$OR_9$, wherein i is an integer from 1 to 3 and wherein k is an integer from 1 to 4, $R_9$ is linear or branched $C_1$-$C_3$ alkyl, or $R_x$ and $R_y$ independently of each other together with the nitrogen atom form a morpholine, a piperidine or a pyrrolidine ring: and wherein $M_1$ represents the corresponding cationic charge equivalent selected from the cations $H^+$, alkali metal cation, $Ca^{2+}$, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p^+$ with $R_{10}$ being $C_1$-$C_4$ alkyl and $R_{11}$ being $C_2$-$C_3$ hydroxyalkyl, wherein both o and p are an integer of 1 or 2 and o≠p, and alkyl is linear or branched; and mixtures of said cations.

24. The cellulose-based material of claim 23, wherein said composition comprises the compound of formula (1a):

(1a)

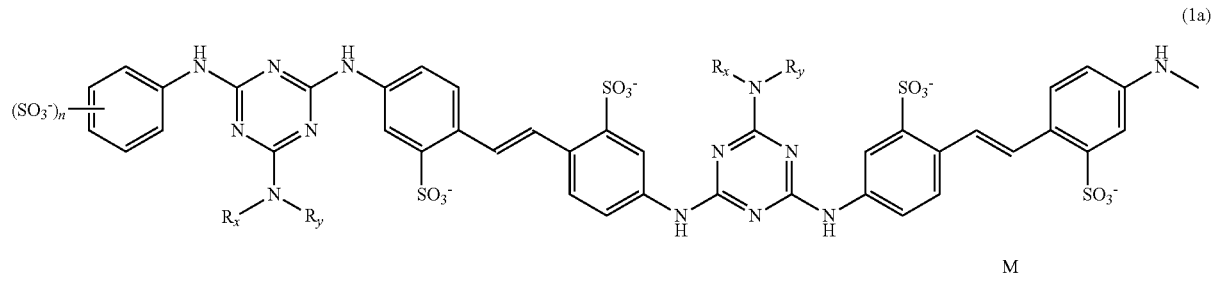

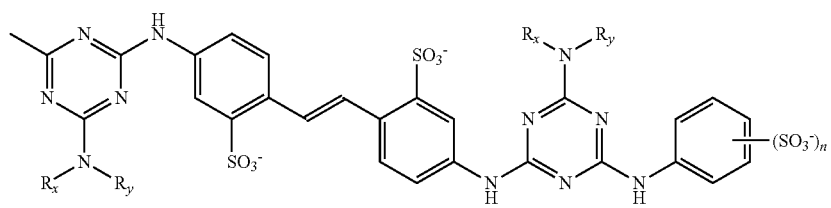

wherein n is 0, 1, or 2; and M represents the corresponding cationic charge equivalent selected from the cations $H^+$, alkali metal cation, $Ca^{2+}$, $Mg^{2+}$, ammonium, $C_1$-$C_4$ tetraalkyl ammonium, ammonium which is mono-, di-, tri- or tetra-substituted by $C_2$-$C_3$ hydroxyalkyl radicals, and $NH(R_{10})_o(R_{11})_p{}^+$ with $R_{10}$ being $C_1$-$C_4$ alkyl and $R_{11}$ being $C_2$-$C_3$ hydroxyalkyl, wherein both o and p are an integer of 1 or 2, and o≠p, alkyl is linear or branched; and mixtures of said cations, and wherein $R_x$ and $R_y$ independently of each other are H, linear or branched $C_1$-$C_4$ alkyl, linear or branched $C_2$-$C_4$ hydroxyalkyl, linear or branched $C_1$-$C_4$ alkoxyalkyl, linear or branched $C_2$-$C_4$ cyanoalkyl, or —$(CH_2)_i$—$SO_3{}^-$, —$(CH_2)_i$-phenyl, —$(CH_2)_k$—COOM, —$(CH_2)_k$—COOR$_9$, —$(CH_2)_k$—CONH$_2$, —$(CH_2)_k$—OR$_9$, wherein i is an integer from 1 to 3 and wherein k is an integer from 1 to 4, $R_9$ is linear or branched $C_1$-$C_3$ alkyl, or $R_x$ and $R_y$ independently of each other together with the nitrogen atom form a morpholine, a piperidine or a pyrrolidine ring.

\* \* \* \* \*